US011576892B2

(12) United States Patent
Cheneval et al.

(10) Patent No.: US 11,576,892 B2
(45) Date of Patent: Feb. 14, 2023

(54) BENZOPYRAN DERIVATIVES AND USES THEREOF

(71) Applicant: Novation Pharmaceuticals Inc., Burnaby (CA)

(72) Inventors: Dominique J. Cheneval, Burnaby (CA); Tania Kastelic, Burnaby (CA)

(73) Assignee: NOVATION PHARMACEUTICALS INC., Burnaby (CA)

( * ) Notice: Subject to any disclaimer, the term of this patent is extended or adjusted under 35 U.S.C. 154(b) by 0 days.

(21) Appl. No.: 15/753,869

(22) PCT Filed: Aug. 17, 2016

(86) PCT No.: PCT/CA2016/050967
§ 371 (c)(1),
(2) Date: Feb. 20, 2018

(87) PCT Pub. No.: WO2017/027973
PCT Pub. Date: Feb. 23, 2017

(65) Prior Publication Data
US 2022/0016071 A1    Jan. 20, 2022

Related U.S. Application Data

(60) Provisional application No. 62/206,538, filed on Aug. 18, 2015.

(51) Int. Cl.
*A61P 29/00* (2006.01)
*A61K 31/352* (2006.01)

(52) U.S. Cl.
CPC ............ *A61K 31/352* (2013.01); *A61P 29/00* (2018.01)

(58) Field of Classification Search
CPC .............................. A61P 29/00; A61K 31/352
See application file for complete search history.

(56) References Cited

U.S. PATENT DOCUMENTS 7,345,090 B2   3/2008  Pfluecker et al.
8,877,795 B2   11/2014 Graef et al.

FOREIGN PATENT DOCUMENTS

| CA | 2356621 | 12/1999 |
|---|---|---|
| CA | 2562763 | 7/2006 |
| CA | 2709784 | 7/2009 |
| CA | 2795350 | 10/2011 |
| EP | 0296122 | 12/1988 |
| KR | 101363472 | 2/2014 |
| WO | 2000039314 | 7/2000 |
| WO | 2009077173 | 6/2009 |
| WO | 2012170371 | 12/2012 |
| WO | 2014095875 | 6/2014 |
| WO | 2017027973 | 2/2017 |

OTHER PUBLICATIONS

Vasilyev et al., Khimiko-Farmatsevticheskii Zhurnal (1991), 25(11), 50-55.*
Isomer, 2019, https://en.wikipedia.org/wiki/Isomer.*
CardiovascularDisease, 2019, https://www.mayoclinic.org/diseases-conditions/heart-disease/symptoms-causes/syc-20353118.*
RespiratoryDiseases, 2019, https://www.unitypoint.org/homecare/article.aspx?id=2448b930-1451-43e4-8634-c0c16707c749.*
AutoimmuneDiseases, 2019, https://www.webmd.com/a-to-z-guides/autoimmune-diseases.*
Vasilyev et al.-abstract, caplus abstractor Khimiko-Farmatsevticheskii Zhurnal (1991), 25(11), 50-55.*
Lee et al., caplus abstract, 2012:1502882.*
Volkova et al., caplus abstract, 2011:601893.*
Zhao et al., caplus abstract, 2005:358077.*
Alley, Michael C. et al., Feasibility of Drug Screening with Panels of Human Tumor Cell Lines Using a Microculture Tetrazolium Assay, Cancer Research, Feb. 1, 1988, pp. 589-601, 48-3.
Benson, Jaqueline M. et al., Therapeutic targeting of the IL-12/23 pathways: generation and characterization of ustekinumab, Nature Biotechnology, Jul. 2011, pp. 615-624, 29-7.
Berge, Stephen M. et al., Pharmaceutical Salts, Pharmaceutical Sciences, Jan. 1977, pp. 1-19, 66-1.
Chang, Qing et al., The IL-6 feed-forward loop: A driver of tumorigenesis, Seminars in Immunology, Feb. 2014, pp. 48-53, 26-1.
Chin, Jennie R. et al., Stromelysin, a Connective Tissue-degrading Metalloendopeptidase Secreted by Stimulated Rabbit Synovial Fibroblasts in Parallel with Collagenase, Journal of Biological Chemistry, Oct. 5, 1985, pp. 12367-12376, 260-22.
Didiot, Marie-Cecile et al., Identification of Cardiac Glycoside Molecules as Inhibitors of c-Myc IRES-Mediated Translation, Journal of Biomolecular Screening, Nov. 13, 2012, pp. 407-419, 18-4.
Supplementary Materials and Methods for Didiot, Marie-Cecile et al., Identification of Cardiac Glycoside Molecules as Inhibitors of c-Myc IRES-Mediated Translation, Journal of Biomolecular Screening, Nov. 13, 2012, pp. 407-419, 18-4.
Dinarello, Charles A., lnterieukin-1, Cytokine & Growth Factor Reviews, Dec. 1997, pp. 253-265, 8-4.
Idziorek, Thierry et al., YOPRO-1 permits cytofluorometric analysis of programmed cell death (apoptosis) without interfering with cell viability, Journal of Immunological Methods, 1995, pp. 249-258, 185-2.
Mak, Isabella W.Y. et al., The effect of the fungal metabolic radicicol analog A on mRNA degradation, Genomics, Dec. 2007, pp. 723-732, 90-6.

(Continued)

*Primary Examiner* — Sun Jae Yoo
(74) *Attorney, Agent, or Firm* — Robert A. Nissen

(57) ABSTRACT

The present disclosure provides for compounds useful for the treatment or prevention of disorders with an etiology associated with or comprising excessive cytokine or chemokine release. The compounds are also useful for the treatment of cancer, inflammatory disorders and disorders associated with an increased stability or translation of mRNA which has an mRNA instability sequence.

6 Claims, 2 Drawing Sheets
Specification includes a Sequence Listing.

(56) References Cited

OTHER PUBLICATIONS

Nishimoto, Norihiro et al., Inhibition of IL-6 for the treatment of inflammatory diseases, Current Opinion in Pharmacology, Aug. 2004, pp. 386-391, 4-4.

Oppmann, Birgit et al., Novel p19 Protein Engages IL-12p40 to Form a Cytokine, IL-23, with Biological Activities Similar as Well as Distinct from IL-12, Immunity, Nov. 2000, pp. 715-725, 13-5.

Schnyder, J. et al., Inhibition of interleukin-1 release by IX 207-887, Agents and Actions, Jun. 1990, pp. 350-362, 30-3-4.

Schnyder, Jorg et al., Spectrophotometric Method to Quantify and Discriminate Urokinase and Tissue-Type Plasminogen Activators, Analytical Biochemistry, Jan. 1992, pp. 156-162, 200-1.

Schoenborn, Jamie R. et al., Regulation of Interferon-gamma During Innate and Adaptive Immune Responses, Advances in Immunology, 2007, pp. 41-101, 96.

Schroder, Kate et al., Interferon-gamma: an overview of signals, mechanisms and functions, Journal of Leukocyte Biology, Feb. 2004, pp. 163-189, 75-2.

Singer, Victoria L. et al., Characterization of PicoGreen Reagent and Development of a Fluorescence-Based Solution Assay for Double-Stranded DNA Quantitation, Analytical Biochemistry, Jul. 1997, pp. 228-238, 249-2.

Tsuchiya, Shigeru et al., Establishment and Characterization of a Human Acute Monocytic Leukemia Cell Line (THP-1), International Journal of Cancer, Aug. 15, 1980, pp. 171-176, 26-2.

Venkiteshwaran, Adith, Tocilizumab, mAbs, Sep. 1, 2009, pp. 432-438, 1-5.

Vom Berg, Johannes et al., Inhibition of IL-12/IL-23 signaling reduces Alzheimer's disease-like pathology and cognitive decline, Nature Medicine, Dec. 2012, pp. 1812-1819, 18-12.

Waldner, Maximilian J. et al., Interleukin-6—A Key Regulator of Colorectal Cancer Development, International Journal of Biological Sciences, 2012, pp. 1248-1253, 8-9.

English translation of patent KR101363472: Lee, Sunkyung et al., The chromene derivative, which is novel its pharmaceutically acceptable salt or its isomer, and the pharmaceutical composition for the prevention or treatment of the manufacturing method thereof and PAR-1 related disease including the same, published Feb. 17, 2014.

Shokol, T.V. et al., 7-Hydroxy-3-Phenoxy-Formylchromones, Analogs of Natural Flavonoids, Chemistry of Natural Compounds, 2009, pp. 350-355, 45-3.

Tetko, I. V. et al., Evolutionary computation for revealing structure-activity relationships in 3-phenoxychromone and 3-phenoxy-4-hydroxycoumarin derivatives, Bioorganicheskaya Khimiya, 1995, pp. 809-815, 21-10.

Vasil'Ev, S.A. et al., Development of Structure—Activity Trends in the Series of 3-Phenoxychromone Derivatives, Pharmaceutical Chemistry Journal, Nov. 1991, pp. 816-821, 25-11. Translated from Khimiko-Famnatsevitcheskii Zhurnal, Nov. 1991, pp. 50-55, 25-11.

Vasil'Ev, S.A. et al., Synthesis and Biological Properties of 3-Phenoxchromones and 3-Phenoxy-4-Hydroxy-7-Methoxycoumarin, Pharmaceutical Chemistry Journal, Jul. 1991, pp. 470-475, 25-7. Translated from Khimiko-Farmatsevitcheskii Zhumal, Jul. 1991, pp. 34-38, 25-7.

Ferrari, Christina et al., Pharmacophore model for bile acids recognition by the FPR receptor, Journal of Computer-Aided Molecular Design, May 2006, pp. 295-303, 20-5.

International Search Report, International Application No. PCT/CA2016/050967, dated Jan. 2015, 8 pages.

\* cited by examiner

BENZOPYRAN DERIVATIVES AND USES THEREOF

CROSS-REFERENCE TO SEQUENCE LISTING

This application incorporates by reference the material in the attached ASCII text file, which is called "sequence_listing_ST25", created Sep. 15, 2016, 1457 bytes in size.

TECHNICAL FIELD

The present disclosure relates to biologically active benzopyran derivatives and analogs for use in the treatment and prophylaxis of inflammatory and other diseases. In some embodiments the disclosure relates to a class of compounds, which affect the stability, or translatability of mRNA that contain one or more mRNA instability sequence and compounds that downregulate protein levels of cytokines and chemokines.

BACKGROUND

A number of compounds have been described in the literature that can modulate mRNA function. One of the first examples of such an effect was Radicicol analog A, which was shown to induce a rapid mRNA degradation of IL-1β, TNFα, IL-6 and Cox-2 in THP-1 cells. It was then demonstrated that the effect of this compound is mediated by the presence of AU-rich elements (ARE) in the target mRNA 3'UTRs. Furthermore, other molecules are used therapeutically in a variety of disease areas are known to affect mRNA stability/translatability such as paclitaxel, cyclosporin A, thalidomide and glucocorticoids.

SUMMARY

In some cases, compounds of the present disclosure modulate post-transcriptional expression of proteins and may be used to treat diseases mediated by these factors. In some cases, compounds of the present disclosure one or more of induce degradation of mRNAs or prevent translation of mRNAs. In some cases, compounds of the present disclosure are used for treatment of diseases and medical conditions which involve increased or prolonged stability or expression of such mRNAs. In some cases the present disclosure provides for the novel and unexpected finding of new classes of compounds capable of inducing degradation, or preventing translation, of mRNAs that contain one or more mRNA instability sequences (together "compound(s) of the present disclosure") involved in the creation or maintenance of inflammatory disease.

In one aspect the present disclosure provides for a method for the prophylaxis or treatment of a disease or medical condition having an etiology associated with the increased stability or translation of mRNA which contains one or more mRNA instability sequences, comprising administration to a human or animal patient an effective amount of a compound which induces degradation or prevents translation of the mRNA, when the disease or medical condition is one with an etiology associated with or comprising excessive inflammation due to cytokine release, particularly IFNγ, IL-6, IL-12, IL-17, IL-23 or IL-1β, such as rheumatoid arthritis, osteoarthritis, septic shock, psoriasis, atherosclerosis, inflammatory bowel disease, Hemophagocytic lymphohistiocytosis (HLH), Crohn's disease, atopic dermatitis, Castleman's disease, multiple sclerosis, Alzheimer's disease and asthma as well as diabetic macular edema.

In some embodiments, the compound is a benzopyran derivative generally described by a compound of formula I:

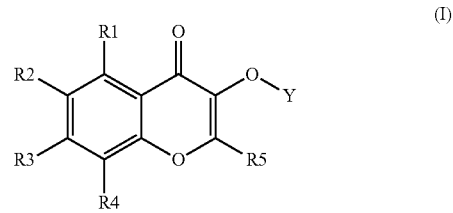

(I)

including pharmaceutically acceptable salts, pharmaceutically active metabolites, pharmaceutically acceptable solvates, pharmaceutically acceptable prodrugs, hydrates, isomers, or stereoisomers thereof, and wherein: each of R1, R2, R3, R4, and R5 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, $O(C_1$-$C_4)$ alkyl, $O(C_1$-$C_4)$ alkenyl, $O(C_2$-$C_4)$ alkoxy, $O(C_1$-$C_4)$ alkyl-COO—, CN, alkyl-CONH, O-alkyl-CONH, or an organic group; wherein, Y is:

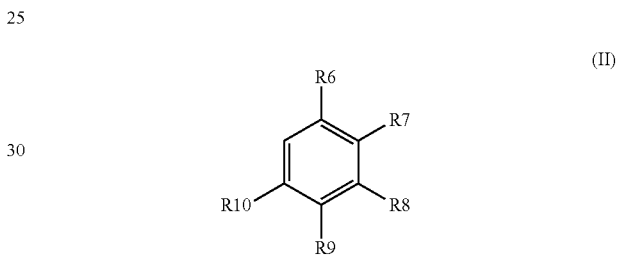

(II)

each of R6, R7, R9, and R10 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, $O(C_1$-$C_4)$ alkyl, $O(C_1$-$C_4)$ alkenyl, $O(C_2$-$C_4)$ alkoxy, $O(C_1$-$C_4)$ alkyl-COO—, CN, or an organic group; and R8 is H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, $O(C_1$-$C_4)$ alkyl, $O(C_1$-$C_4)$ alkenyl, $O(C_2$-$C_4)$ alkoxy, $O(C_1$-$C_4)$ alkyl-COO—, CN, an organic group, or CONR11R12, wherein R11 is H or ($C_1$-$C_4$) alkyl and R12 is H or ($C_1$-$C_4$) alkyl.

In various embodiments, there may be included any one or more of the following features: One or more of the compounds disclosed here for use in the treatment of any one or more of the diseases, conditions, inhibitions, or other action steps disclosed here. One or more of the compounds disclosed here for use as a medicament—a compound for use as a medicament, for example for treatment of any one or more of the conditions or diseases disclosed here. A pharmaceutical composition comprising one or more of the compounds disclosed here. In some embodiments, the compound is used in the treatment of inflammatory disease. In some embodiments, the compound is an anti-inflammatory agent. In some embodiments, the compound is used to inhibit the release of a cytokine. In some embodiments, the cytokine is a chemokine. In some embodiments, the cytokine is an interleukin. In some embodiments, the interleukin is selected from the group comprising IL-1, IL-1β, IL-2, IL-4, IL-5, IL-6, IL-10, IL-12, IL-17, or IL-23. In some embodiments, the cytokine is an interferon. In some embodiments, the interferon is IFN-γ. In some embodiments, the compound down-regulates the translation of an mRNA that codes for the cytokine. In some embodiments, the mRNA comprises an instability sequence. In some embodiments, the instability sequence comprises an adenine/uracil (AU)-rich element. In some embodiments, adenine/uracil (AU)-rich element comprises one or more of the following sequences: AUUUA, UAUUUAU, UUAUUUA(U/A)(U/A), or AUUUAUUUA. In some embodiments, the compound is selected to bind or interact with, directly or indirectly through other proteins, to the adenine/uracil (AU)-rich element. In some embodiments, the compound is selected to bind to the adenine/uracil (AU)-rich element. In some embodiments, the compound is used to treat one or more of rheumatoid arthritis, osteoarthritis, septic shock, psoriasis, atherosclerosis, inflammatory bowel disease, hemophagocytic lymphohistiocytosis, Crohn's disease, atopic dermatitis, Castleman's disease, multiple sclerosis, Alzheimer's disease, asthma, diabetic macular edema, excessive inflammation due to cytokine release, acute inflammation, chronic inflammation, autoimmune diseases, respiratory diseases, infectious diseases, transplant rejection, neuronal inflammation, cardiovascular diseases, multiple myeloma, colorectal cancer, pathological conditions associated with abnormal cell proliferation, abnormal cell proliferation of malignant cells of muscle, bone, connective tissues, skin, the brain, lungs, sex organs, lymphatic systems, renal systems, mammary cells, blood cells, the liver, the digestive tract, the pancreas, thyroid glands, or adrenal glands, solid tumors, cancers of the ovary, breast, brain, prostate, colon, stomach, kidney, or testicles, Kaposi's sarcoma, cholangioma, chorioma, neuroblastoma, Wilms' tumor, Hodgkin's disease, melanomas, lymphatic leukemias, acute or chronic granulocytic lymphomas, oncogene mediated cancers and malignant diseases, tumor growth, metastasis invasion, or multidrug resistance. In some embodiments, a medicament comprising a pharmaceutically acceptable carrier and the compound is used for the treatment of inflammatory disease. In some embodiments, the pharmaceutically acceptable carrier comprises one or more of a filler, a binder, a disintegrator, a flow conditioner, a coating, or a lubricant. In some embodiments, the filler comprises one or more of a sugar, a cellulose preparation, or a calcium phosphate. In some embodiments, the binder comprises one or more of a starch, methylcellulose, hydroxypropylmethylcellulose, sodium carboxymethylcellulose, or polyvinylpyrrolidone. In some embodiments, the disentegrator comprises one or more of a starch, crosslinked polyvinylpyrrolidone, alginic acid, or a salt. In some embodiments the coating comprises one or more of a sugar, gum arabic, talc, polyvinylpyrrolidone, polyethylene glycol, titanium dioxide, acetylcellulose phthalate, or hydroxypropylmethylcellulose phthalate. In some embodiments, the compound is present in the amount of 1-95% of the weight of the medicament. In some embodiments, the compound is present in the amount of 20-90% of the weight of the medicament. In some embodiments, the medicament is a capsule comprising 0.05-1.0 g of the compound. In some embodiments, the medicament is in one or more of the following forms: orally administrable, injectable, suppository, or skin ointment. In some embodiments, the medicament comprises one or more of a polyamine synthesis inhibitor, a protein kinase C inhibitor, a tyrosine kinase inhibitor, a cytokine inhibitor, a negative growth regulator, an aromatase inhibitor, an anti-estrogen agent, a cytotoxic agent, or a cytostatic agent. R1, R2, R4, R5, R6, R7, R9, R10 is H. R3 is OOCCH$_3$ or OH, and R8 is COO, H, COOCH$_3$, or OCH$_3$. The compound is:

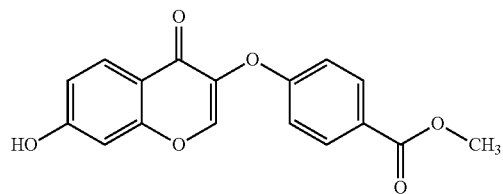

(IV)

In a further aspect the present disclosure provides use of a compound of Formula I which induces degradation of mRNA which contains one or more mRNA instability sequences, for the preparation of a medicament for use in the treatment or prophylaxis of a disease or medical condition having an etiology associated with the increased stability of mRNA which contains one or more mRNA instability sequences, when the disease or medical condition is one with an etiology associated with or comprising excessive cytokine release, particularly IFNγ, IL-6, IL-12, IL-17, IL-23 or IL-1γ, such as rheumatoid arthritis, osteoarthritis, septic shock, psoriasis, atherosclerosis, inflammatory bowel disease, Hemophagocytic lymphohistiocytosis (HLH), Crohn's disease, atopic dermatitis, Castleman's disease, multiple sclerosis, Alzheimer's disease and asthma as well as diabetic macular edema.

In a still further aspect, the present disclosure provides a method for inducing degradation of mRNA, or inhibiting translation of an mRNA in a patient, which comprises administration of an effective amount of a compound of Formula I, which induces mRNA degradation or prevents mRNA translation to the patient, wherein the mRNA contains an mRNA instability sequence, when the mRNA is coding for IFNγ, IL-6, IL-12, IL-17, IL-23 or IL-1β. In a still further aspect, the present disclosure provides use of a compound of Formula I which induces mRNA degradation or inhibits translation of an mRNA; in the preparation of a medicament for use in inducing degradation of mRNA which contains a mRNA degradation sequence in a patient, when the mRNA is mRNA coding for IFNγ, IL-6, IL-12, IL-17, IL23 or IL-1β. The present disclosure further provides the use of a compound of Formula I for preparation of a medicament for treatment of a cancer and/or malignant disease. The present disclosure also provides a method for the prophylaxis or treatment of a cancer and/or malignant disease comprising administration to a patient an effective amount of a compound of Formula I.

In another embodiment, each of R1, R2, R3, R4, and R5 are, independently from each other, H, OH, NO$_2$, COOCH$_3$, COOH, halogen, (C$_1$-C$_4$) alkyl, (C$_1$-C$_4$) alkenyl, (C$_1$-C$_4$) alkoxy, (C$_1$-C$_4$) alkyl-COO—, OCOCH$_3$, O(C$_1$-C$_4$) alkyl, O(C$_1$-C$_4$) alkenyl, O(C$_2$-C$_4$) alkoxy, O(C$_1$-C$_4$) alkyl-COO—, CN, alkyl-CONH, or O-alkyl-CONH; and each of R6, R7, R9, and R10 are, independently from each other, H, OH, NO$_2$, COOCH$_3$, COOH, halogen, (C$_1$-C$_4$) alkyl, (C$_1$-C$_4$) alkenyl, (C$_1$-C$_4$) alkoxy, (C$_1$-C$_4$) alkyl-COO—, OCOCH$_3$, O(C$_1$-C$_4$) alkyl, O(C$_1$-C$_4$) alkenyl, O(C$_2$-C$_4$) alkoxy, O(C$_1$-C$_4$) alkyl-COO—, or CN; and R8 is H, OH, NO$_2$, COOCH$_3$, COOH, halogen, (C$_1$-C$_4$) alkyl, (C$_1$-C$_4$) alkenyl, (C$_1$-C$_4$) alkoxy, (C$_1$-C$_4$) alkyl-COO—, OCOCH$_3$, O(C$_1$-C$_4$) alkyl, O(C$_1$-C$_4$) alkenyl, O(C$_2$-C$_4$) alkoxy, O(C$_1$-C$_4$) alkyl-COO—, CN, or CONR11R12, wherein R11 is H or (C$_1$-C$_4$) alkyl and R12 is H or (C$_1$-C$_4$) alkyl.

In some embodiments, the compound comprises Y, wherein R6, R7, R9, and R10 are H, and R8 is H, OH, NO$_2$, COOCH$_3$, COOH, halogen, (C$_1$-C$_4$) alkyl, (C$_1$-C$_4$) alkenyl, ($C_1$-$C_4$) alkoxy, ($C_1$-$C_4$) alkyl-COO—, OCOCH$_3$, O($C_1$-$C_4$) alkyl, O($C_1$-$C_4$) alkenyl, O($C_2$-$C_4$) alkoxy, O($C_1$-$C_4$) alkyl-COO—, CN, an organic group, or CONR11R12, wherein R11 is H or ($C_1$-$C_4$) alkyl and R12 is H or ($C_1$-$C_4$) alkyl. In some embodiments, the compound comprises Y, wherein R6, R7, R9, and R10 are H, and R8 is H, OH, NO$_2$, COOCH$_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, OCOCH$_3$, O($C_1$-$C_4$) alkyl, O($C_1$-$C_4$) alkenyl, O($C_2$-$C_4$) alkoxy, O($C_1$-$C_4$) alkyl-COO—, CN, or CONR11R12, wherein R11 is H or ($C_1$-$C_4$) alkyl and R12 is H or ($C_1$-$C_4$) alkyl.

In some embodiments, the compound is selected from the following group of compounds:

1 (333)
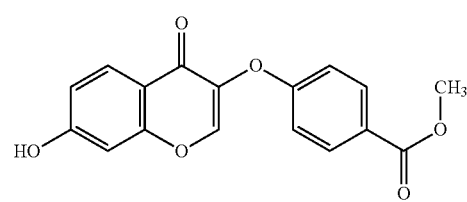

2
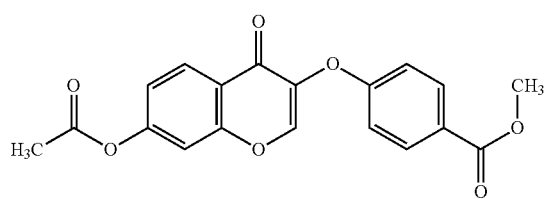

3 (1781)
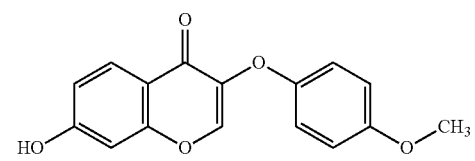

4
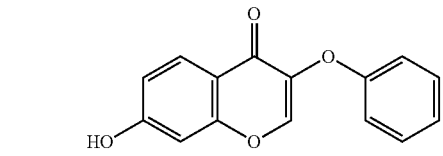

5
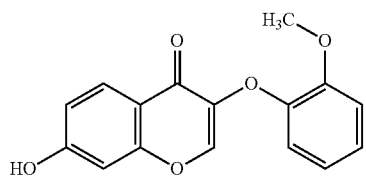

6
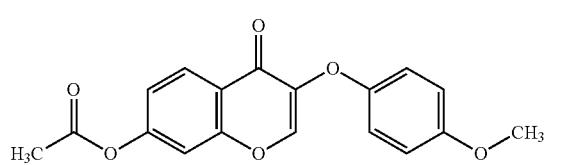

7
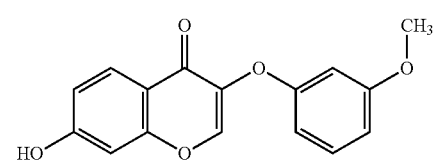

8 (1782)
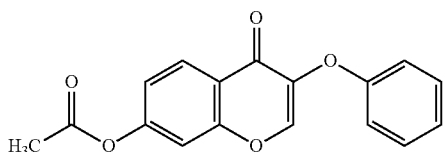

9
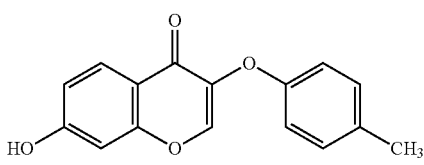

10
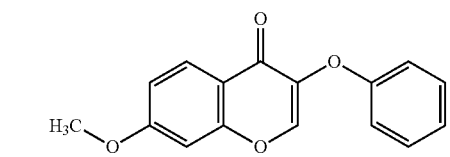

11
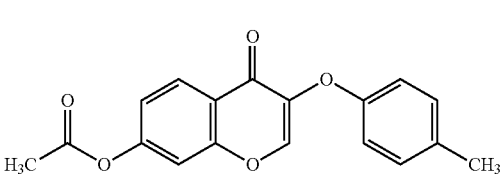

12
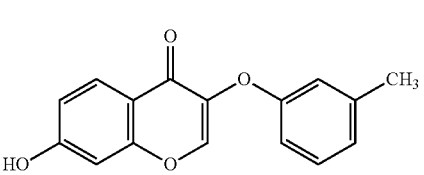

13
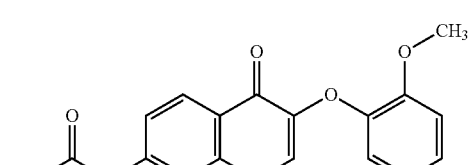

14
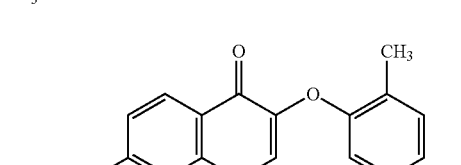

15
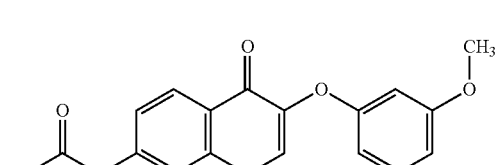

16
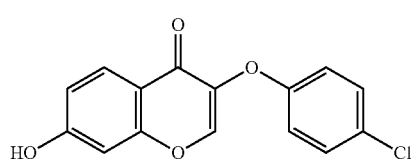

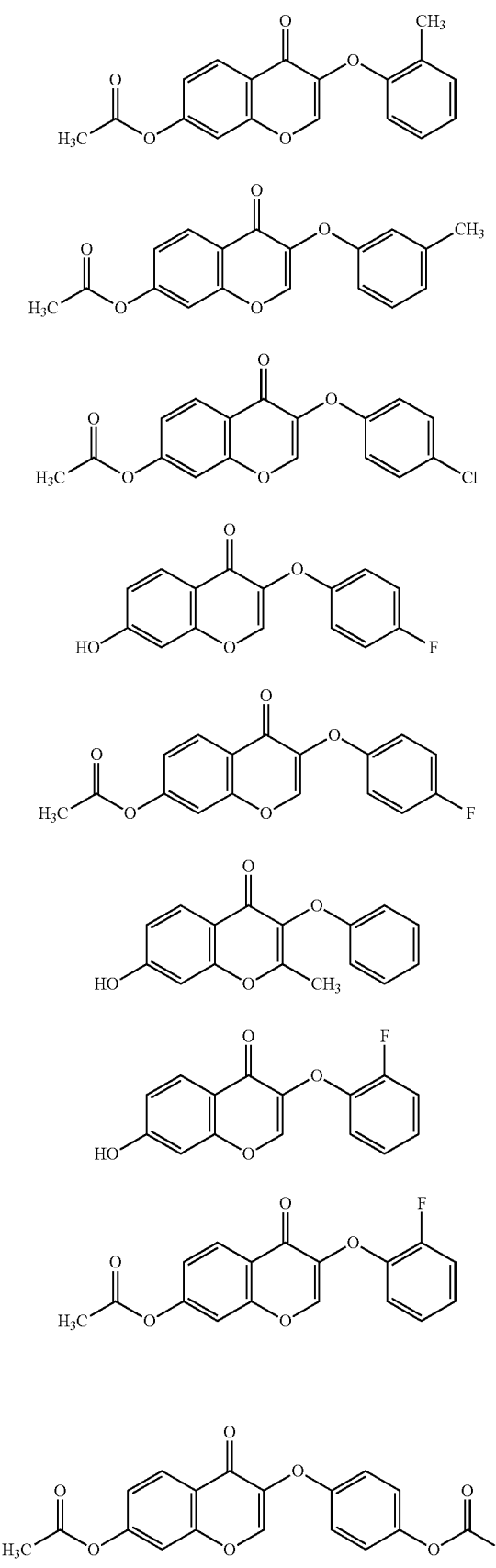
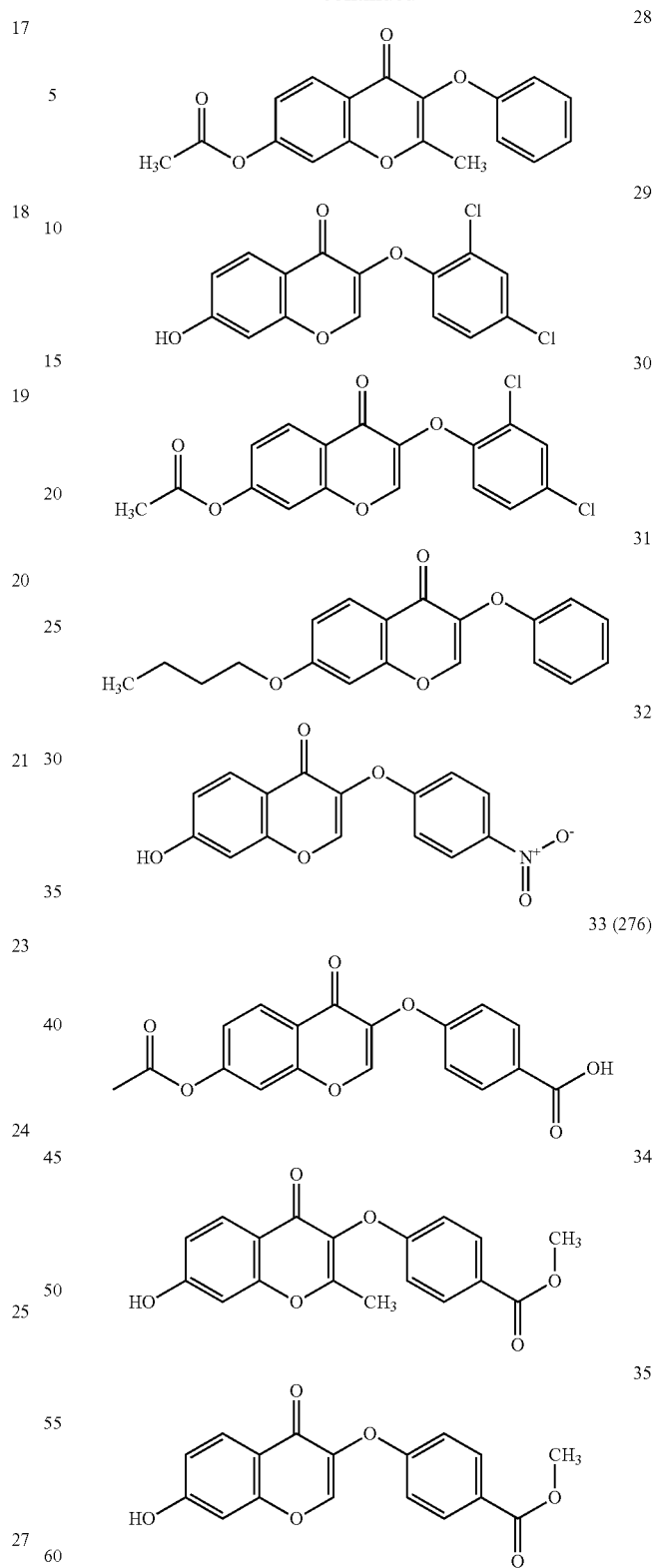
In a further aspect the disclosure provides use of a compound of Formula I which induces degradation of mRNA which contain one or more mRNA instability sequences, for the preparation of a medicament for use in the treatment or prophylaxis of a disease or medical condition having an etiology associated with the increased stability of mRNA which contains one or more mRNA instability sequences, when the disease or medical condition is one with an etiology associated with or comprising excessive cytokine release, particularly IFNγ, IL-6, IL-12, IL-17, IL-23 or IL-1β, such as rheumatoid arthritis, osteoarthritis, septic shock, psoriasis, atherosclerosis, inflammatory bowel disease, Hemophagocytic lymphohistiocytosis (HLH), Crohn's disease, atopic dermatitis, Castleman's disease, multiple sclerosis, Alzheimer's disease and asthma as well as diabetic macular edema.

In a still further aspect, the present disclosure provides a method for inducing degradation of mRNA, or inhibiting translation of an mRNA in a patient; which comprises administration of an effective amount of a compound of Formula I, which induces mRNA degradation or prevents mRNA translation to the patient, wherein the mRNA contains an mRNA instability sequence, when the mRNA is coding for IFNγ, IL-6, IL-12, IL-17, IL-23 or IL-1β.

In a still further aspect, the present disclosure provides use of a compound of Formula I which induces mRNA degradation or inhibits translation of an mRNA; in the preparation of a medicament for use in inducing degradation of mRNA which contains a mRNA degradation sequence in a patient, when the mRNA is mRNA coding for IFNγ, IL-6, IL-12, IL-17, IL-23 or IL-1β.

Some cases of the present disclosure further provide the use of a compound of Formula I for preparation of a medicament for treatment of a cancer and/or malignant disease. Some cases provide a method for the prophylaxis or treatment of a cancer and/or malignant disease comprising administration to a patient an effective amount of a compound of Formula I.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Figure 1:
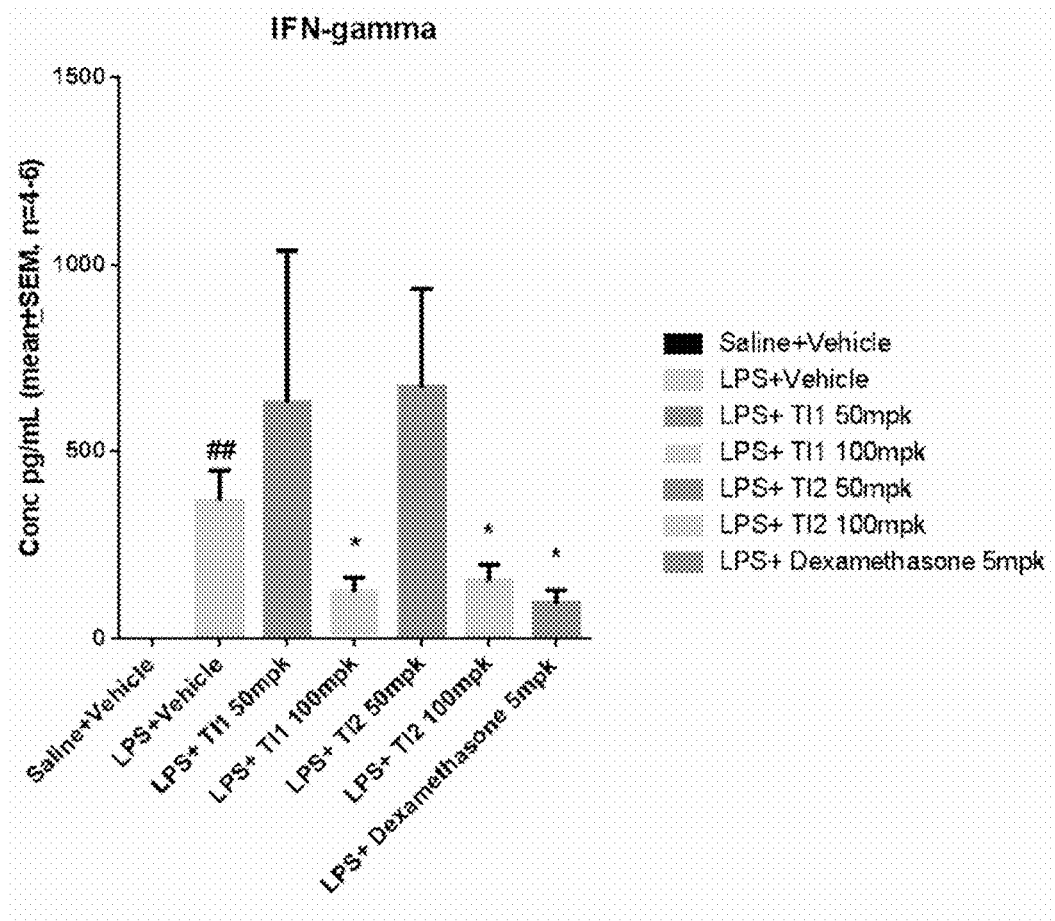
FIG. 1 is a bar graph illustrating the effect of test compounds 333 (TI1) and 1781 (TI2) on IFN-gamma levels in serum of LPS treated mice.

Immaterial modifications may be made to the embodiments described here without departing from what is covered by the claims.

Post-transcriptional regulation of gene expression is an important means for modulating protein levels within the cellular environment. mRNA half-life and translatability plays a critical role in the control of gene expression; and mRNA degradation and translation are highly regulated processes. One particular group of genes controlled in this way are inflammatory cytokines and chemokines. Cytokine or chemokine production is controlled by sequence elements found in the 5' and 3'UTRs of their mRNAs. Therefore, compounds that potentially interact with, or influence regulation occurring through the 5'-UTR and 3'-UTR, or the 5'-UTR or the 3'-UTR of cytokine or chemokine mRNA, may modulate post-transcriptional expression of these proteins, and may be used to treat diseases mediated by these factors.

Gene expression is a highly regulated process in which information flows from the genetic DNA to proteins via intermediate mRNA. Some mRNA is only produced under certain circumstances, when stimulation occurs. Certain other mRNAs, such as that required for quick response situations (e.g. host immune system), are constantly being produced, but kept under control by translational inhibition or rapid degradation until physiologically required, at which time they are stabilized and protein production starts.

It is now known that modulation of mRNA stability is controlled by a natural mechanism wherein certain molecular sequences within the mRNA act as regulators of activity either stimulating degradation or stabilization. Control of mRNA stability as well as translatability is exerted through specific cis-acting elements (stability control elements) and trans-acting factors (mRNA binding proteins). mRNA modulation appears to be the key regulator in controlling many protein targets and impacting disease.

The stability and translatability of mRNA is a major regulatory mechanism involved in the expression of factors as cytokines and chemokines involved with the immune response, growth factors and certain proto-oncogenes. In fact, many such disease relevant mRNAs are regulated through changes in mRNA stability. In the diseased state, mRNA half-life and levels of disease-related factors are significantly increased due to mRNA stabilization.

Regulated mRNA stability or translatability depends on the interaction between intrinsic, cis-acting elements, the sequence itself, and trans-acting factors, factors that can bind the cis-acting elements such as RNA binding proteins and microRNA. The former consist of either highly conserved primary sequences or stable stem-loop structures located in the coding or non-coding regions. The proto-oncogene c-fos mRNA for instance, has a half-life of approximately 30 min. and its instability is modulated by sequences in its 3'UTR. Replacement of the 3'UTR in c-fos mRNA from β-globin, which has a half-life of approximately 24 h, produces a stable chimaeric transcript. Conversely, fusion of the c-fos 3'UTR to β-globin confers instability.

There are a number of trans-acting regulatory factors including several mRNA-binding proteins and microRNAs. A number of these regulatory factors have been shown to be ARE-binding proteins, whereupon binding to mRNA has been show to either stabilize or destabilize their RNA targets or modulate translation from these mRNAs.

A number of signal transduction processes are involved with influencing the association of mRNA binding proteins to mRNA which then alters the mRNA decay rate or influence its translation. Many RNA-binding proteins have been discovered and characterized by the transcripts they bind and their dependence on tissue expression, nucleotide sequence, and cellular stimulation.

Small noncoding RNA can also post-transcriptionally regulate protein expression. MicroRNA 16 (miR16) is involved in regulating TNFα mRNA stability. In addition to influencing mRNA half-life, microRNAs have been reported to enhance translation of TNFα mRNA via its ARE upon serum starvation, an effect that was coupled to two microRNP-related proteins (FXR1 and Ago2). The involvement of microRNA thus connects two post-transcriptional regulatory mechanisms. Thus post-transcriptional regulation of gene expression is a sophisticated and complex process, and as such, achieves a highly specific control over protein production and concurrently, can coordinate the expression of functionally related genes through modulating mRNA stability and translatability.

A number of compounds have been described in the literature that can modulate mRNA function. One of the first examples of such an effect was Radicicol analog A, which was shown to induce a rapid mRNA degradation of IL-1β, TNFα, IL-6 and Cox-2 in THP-1 cells. It was then demonstrated that the effect of this compound is mediated by the presence of AU-rich elements (ARE) in the target mRNA 3'UTRs. Furthermore, other molecules used therapeutically in a variety of disease areas are known to affect mRNA stability/translatability such as paclitaxel, cyclosporin A, thalidomide and glucocorticoids.

The compounds of the present disclosure may induce degradation of mRNA or inhibit translation of an mRNA, which contains a mRNA instability sequence is potentially of interest for use in the present disclosure. Compounds which induce degradation of mRNA or inhibits translation of an mRNA which contains a mRNA instability sequence are hereinafter referred to as compounds for use in the disclosure.

By way of example, Canadian Patent No. 2,356,621 describes a reporter gene assay for the identification of compounds which destabilize mRNA or inhibits translation of an mRNA. In this assay test compounds are contacted with a DNA expression system which in the absence of the compound is capable of expressing a protein having a detectable signal, and wherein the mRNA which codes for the protein and which is transcribed from the expression system comprises at least one copy of a mRNA instability sequence. The detectable signal is measured in the presence of the test compound and the result obtained is compared with a control. Compounds that destabilize mRNAs induce degradation of the mRNA which codes for the detectable signal leading to a decrease in the magnitude of the detectable signal obtained in the reporter gene assay. In a similar way compounds which inhibit translation of an mRNA also lead to a decrease in the magnitude of the detectable signal obtained in the reporter gene assay.

Preferred compounds for use in the present disclosure include compounds that may be identified as inducers of mRNA instability or inhibitors of translation of an mRNA using methods such as the reporter gene assay as described above and as described in more detail in Canadian Patent No. 2,356,621 and as hereinafter described in the Examples. mRNA instability sequences often contain one or more copies of sequence motifs, e.g. selected from: AUUUA, UAUUUAU, UUAUUUA(U/A)(U/A), and AUUUAUUUA. Such sequence motifs are typically in genes between the stop codon and the poly A signal and may associated with appropriate flanking sequences and may interact in combination with other sequences, e.g. present in the 5' UTR and e.g. with instability motifs present in the coding region.

As demonstrated herein, the authors have discovered the novel utility of certain benzopyran derivatives that may act as inducers of degradation of mRNAs or inhibitors of translation from RNAs, which contain mRNA instability sequences. The activity of compounds for use in the disclosure as inducers of mRNA degradation may be demonstrated using assays known to workers skilled in the art, for example by means of a reporter gene assay as described herein, or as described in more detail in Canadian Patent No. 2,356,621.

One method for identifying the ability of a compound of the present disclosure to induce mRNA degradation, comprises i) contacting the compound with a DNA expression system which in the absence of the compound is capable of expressing a protein having a detectable signal, wherein the mRNA which codes for the protein and which is transcribed from the expression system comprises at least one copy of a mRNA instability sequence; ii) measuring the detectable signal in the presence of the test compound and comparing the result obtained with a control. A related method can be used to compare compounds that induce mRNA degradation. This method comprises separately contacting the compounds with a DNA expression system which in the absence of the compounds is capable of expressing a protein having a detectable signal, wherein the mRNA which codes for the protein and which is transcribed from the expression system comprises at least one copy of a mRNA instability sequence, measuring the detectable signal in the presence of each test compound and comparing the signals obtained.

The DNA expression system used in the above described methods typically comprises a gene coding for expression of the protein having a detectable signal, wherein the gene comprises DNA coding for the amino acid sequence of the protein together with associated 5' and 3'UTR sequences comprising appropriate expression control elements including promoter and/or enhancer regions, and characteristically DNA corresponding to at least one copy of a mRNA instability sequence. An exemplary DNA expression system that can be used in the above methods is a cell based expression system, conveniently in the form of a suitably transformed cell line, optionally a stably transformed cell line. The host cell is typically a eukaryotic host cell, in particular an animal host cell such as a mammalian host cell.

The host cell may be of the same general cell type as the cells that express the protein that is coded for by the mRNA which it is desired to destabilize. Thus for instance, if the assay is to be used for the characterization of compounds of the present disclosure to demonstrate their ability to destabilize the mRNA coding for a cytokine, the host cell used is preferably a cell or cell line which is of the same or similar cell type to the cells which normally produce the cytokine in question. For example, monocyte or monocyte-like cell lines such as THP-1 may be used as host cells for assaying for compounds which destabilize cytokines such as e.g. IL-6. Preferred cell lines for oncogene and other cancer related gene mRNA instability assays are, e.g. Colon 205, KB 31, KB 8511, DU145, HCT116, MCF7, MCF7/ADR, MDA-MB-231, MDA-MB-435-and MDA-MB-435/TO.

The gene coding for expression of the protein having a detectable signal may encode a protein that may itself comprise the detectable signal. For instance, the protein may comprise a fluorescent protein, e.g. green fluorescent protein.

Alternatively, the protein is such that it is capable of reacting with an appropriate substrate or other substance to give a detectable signal. Conveniently the protein encoded by the mRNA is an enzyme or enzymatically active fragment of an enzyme. Examples of suitable enzymes include horseradish peroxidase (HRP), chloramphenicol acetyltransferase (CAT), alkaline phosphatase (AP), secreted alkaline phosphatase (SEAP), β-galactosidase, or luciferase. Methods for detecting and quantifying such enzymes are well-known, using appropriate substrates and measurements. It will be appreciated, however, that there are alternative means for detecting and quantifying such enzymes and one skilled in the art will be capable of identifying a suitable protein and measurement procedure that may be used the methods described herein.

Alternative methods for measuring the ability of test molecules to induce mRNA degradation are known to workers skilled in the art and may be used to measure the activity of the benzopyran derivatives of the present disclosure.

Cytokines such as IFNγ, IL-1β, IL-6, IL-12, IL-17 and IL-23 are all pro-inflammatory factors whose expression is upregulated during an inflammatory process. The upregulation is mainly due to a stabilization of their respective mRNAs i.e. increase of mRNA half-life.

THP-1 cells after differentiation with interferon gamma (IFNγ) mimic native monocyte-derived macrophages in several respects, most importantly in becoming responsive to both lipopolysaccharide (LPS) and phorbol-myristate-acetate (PMA) which the secretion of mature cytokines. THP-1 cells thus provide a valuable model system for studying the mechanisms involved in cytokine processing and secretion.

Interferon gamma (IFNγ) is a cytokine produced by activated T and NK cells. IFNγ is important for immunity against viral as well as some bacterial infections. IFNγ is an activator of macrophages and inducer of Class II major histocompatibility complex (MHC) molecule expression (Schroder, Hertzog et al. (2004). Interferon-gamma: an overview of signals, mechanisms and functions. J Leukoc Biol. 75: 163-189.) Aberrant IFNγ expression is associated with a number of autoinflammatory and autoimmune diseases (Schoenborn and Wilson (2007). Regulation of interferon-gamma during innate and adaptive immune responses. Adv Immunol. 96: 41-101.)

Interleukin 1 beta (IL-1β) is a major mediator of inflammation. Together with tumor necrosis factor alpha (TNFα) it contributes to the pathogenesis of inflammation and tissue destruction observed e.g. in the joints of arthritis patients. (Dinarello 1997. Interleukin-1. Cytokine Growth Factor Rev. 8: 253-265.)

Interleukin-6 (IL-6) is a pleiotropic cytokine with various biological activities. Overproduction of IL-6 has been found to play a role in various chronic inflammatory diseases such as e.g. rheumatoid arthritis; but is also implicated in other autoimmune diseases, multiple myeloma, colorectal cancer and prostate cancer, (Nishimoto and Kishimoto (2004). Inhibition of IL-6 for the treatment of inflammatory diseases. Curr Opin Pharmacol. 4: 386-391.), (Waldner, Foersch et al. (2012). Interleukin-6—a key regulator of colorectal cancer development. Int J Biol Sci. 8: 1248-1253.) IL-6 signaling plays a prominent role in tumorigenesis and metastasis and blockade of the IL-6 signaling pathway in pre-clinical models leads to a reduction in tumor growth and metastasis, (Chang, Daly et al. (2014). The IL-6 feed-forward loop: a driver of tumorigenesis. Semin Immunol. 26: 48-53.) Humanized anti-IL-6 receptor (tocilizumab) and anti-IL-6 antibodies have been developed as therapies and have shown to be beneficial in clinical studies, (Venkiteshwaran (2009). Tocilizumab. mAbs, Taylor & Francis. 1: 432-438.)

IL-12 is primarily produced by phagocytic and dendritic cells in response to microbial stimulation and activates natural killer cells, inducing lymphokine-activated killer cells, and triggering IFN-γ production and T-cell proliferation. A heterodimer, IL-12 is comprised by covalently linked p40 and p35 protein subunits. In 2000 Oppmann et al. (Oppmann, Lesley et al. Novel p19 Protein Engages IL-12p40 to Form a Cytokine, IL-23, with Biological Activities Similar as Well as Distinct from IL-12 Immunity, Elsevier. 13: 715-725.) reported the existence of another p40 complex, namely p19p40 and named it IL-23. Subsequent studies revealed that many inflammatory activities previously allotted to IL-12 were actually driven by IL-23 due to the common p40 subunit. Clinical observations established that IL-12/23p40 is integral to the pathologies of psoriasis, psoriatic arthritis and Crohn's disease. (Benson, Sachs et al. (2011). Therapeutic targeting of the IL-12/23 pathways: generation and characterization of ustekinumab. Nat Biotechnol. 29: 615-624). Inhibition of IL-12/IL-23 signaling was also reported to reduce Alzheimer's disease-like pathology and cognitive decline (Vom Berg, Prokop et al. (2012). Inhibition of IL-12/IL-23 signaling reduces Alzheimer's disease-like pathology and cognitive decline. Nat Med. 18: 1812-1819).

As used herein, an "effective amount" is an amount of a compound of the present disclosure sufficient to achieve the intended purpose. For example, an effective amount of a compound of the present disclosure to ameliorate inflammatory disease, is an amount sufficient, in vivo, to result in an reducing the inflammatory mediators, as known in the art, or known inflammatory cytokines and other inflammatory mediators including, but not limited to, those listed herein. An effective amount of a compound of the present disclosure to treat or inflammatory disease is an amount of the compound of the present disclosure sufficient to reduce or remove the symptoms of inflammation. The effective amount of a given compound of the present disclosure will vary with factors such as the nature of the agent, the route of administration, the size and species of the animal or patient to receive the therapeutic agent, and the purpose of the administration. The effective amount in each individual case may be determined empirically by a skilled artisan according to established methods in the art and the teachings herein.

As used herein, "administration" means the introduction of a compound to a mammal, for example a human, either systemically or localized to an organ or tissue, through means generally known in the art, such that the administered compound is capable of interacting with the general tissue or organ, or cells of interest. Examples of such means generally known in the art include, but are not limited to, oral formulations, intravenous injection, topical applications, catheterization, suppository, and direct introduction to a tissue through injection.

The phrase "pharmaceutically acceptable salt(s)", as used herein, means those salts of compounds of the present disclosure that retain the biological effectiveness and properties of the free acids or free bases and that are not otherwise unacceptable for pharmaceutical use. Pharmaceutically acceptable salts of compounds of the present disclosure include salts of acidic or basic groups which may be present in the compounds of the present disclosure. Derivatives of compounds of the present disclosure that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. compounds of the present disclosure that include an amino moiety can also form pharmaceutically acceptable salts with various amino acids, in addition to the acids mentioned above. Compounds of the present disclosure that are acidic in nature are capable of forming a wide variety of salts with various inorganic and organic bases. Suitable base salts are formed from bases that donate cations to form non-toxic salts, suitable cations include, but are not limited to, sodium, aluminum, calcium, lithium, magnesium, potassium, zinc and diethanolamine salts. For a review on pharmaceutically acceptable salts see Berge et al, J. Pharm. Set, 66, 1-19 (1977), incorporated herein by reference.

A pharmaceutically acceptable prodrug includes physiologically acceptable and hydrolysable esters, and other suitable compounds that react within the body to form the disclosed compounds. A pharmaceutically active metabolite includes a compound that is metabolized in the body to produce the disclosed compounds.

Preferred compounds for use in the present disclosure include compounds, which may be identified as modulators of mRNA using the reporter gene assay as described above and as hereinafter described in the Examples. Particular examples of compounds for use in the present disclosure include methyl 4-[(7-hydroxy-4-oxo-4H-chromen-3-yl)oxy]benzoate and analogs.

A particular class of analogs which includes compounds for use in the disclosure are compounds of formula I:

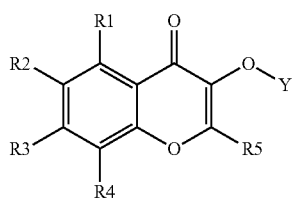

including pharmaceutically acceptable salts, pharmaceutically active metabolites, pharmaceutically acceptable solvates, pharmaceutically acceptable prodrugs, hydrates, isomers, or stereoisomers thereof, and wherein: each of $R1$, $R2$, $R3$, $R4$, and $R5$ are, independently from each other, H, OH, $NO_2$, $COOCH_3$, COOH, halogen, $(C_1-C_4)$ alkyl, $(C_1-C_4)$ alkenyl, $(C_1-C_4)$ alkoxy, $(C_1-C_4)$ alkyl-COO—, $OCOCH_3$, $O(C_1-C_4)$ alkyl, $O(C_1-C_4)$ alkenyl, $O(C_2-C_4)$ alkoxy, $O(C_1-C_4)$ alkyl-COO—, CN, alkyl-CONH, O-alkyl-CONH, or an organic group; wherein, Y is:

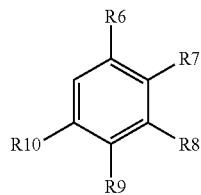

wherein each of $R6$, $R7$, $R9$, and $R10$ are, independently from each other, H, OH, $NO_2$, $COOCH_3$, COOH, halogen, $(C_1-C_4)$ alkyl, $(C_1-C_4)$ alkenyl, $(C_1-C_4)$ alkoxy, $(C_1-C_4)$ alkyl-COO—, $OCOCH_3$, $O(C_1-C_4)$ alkyl, $O(C_1-C_4)$ alkenyl, $O(C_2-C_4)$ alkoxy, $O(C_1-C_4)$ alkyl-COO—, CN, or an organic group; and $R8$ is H, OH, $NO_2$, $COOCH_3$, COOH, halogen, $(C_1-C_4)$ alkyl, $(C_1-C_4)$ alkenyl, $(C_1-C_4)$ alkoxy, $(C_1-C_4)$ alkyl-COO—, $OCOCH_3$, $O(C_1-C_4)$ alkyl, $O(C_1-C_4)$ alkenyl, $O(C_2-C_4)$ alkoxy, $O(C_1-C_4)$ alkyl-COO—, CN, an organic group, or CONR11R12, wherein R11 is H or $(C_1-C_4)$ alkyl and R12 is H or $(C_1-C_4)$ alkyl. In some cases R6, R7, R9, and R10 are H, and R8 is H, OH, $NO_2$, $COOCH_3$, COOH, halogen, $(C_1-C_4)$ alkyl, $(C_1-C_4)$ alkenyl, $(C_1-C_4)$ alkoxy, $(C_1-C_4)$ alkyl-COO—, $OCOCH_3$, $O(C_1-C_4)$ alkyl, $O(C_1-C_4)$ alkenyl, $O(C_2-C_4)$ alkoxy, $O(C_1-C_4)$ alkyl-COO—, CN, an organic group, or CONR11R12, wherein R11 is H or $(C_1-C_4)$ alkyl and R12 is H or $(C_1-C_4)$ alkyl. In some embodiments, the compound comprises Y, wherein R6, R7, R9, and R10 are H, and R8 is H, OH, $NO_2$, $COOCH_3$, COOH, halogen, $(C_1-C_4)$ alkyl, $(C_1-C_4)$ alkenyl, $(C_1-C_4)$ alkoxy, $(C_1-C_4)$ alkyl-COO—, $OCOCH_3$, $O(C_1-C_4)$ alkyl, $O(C_1-C_4)$ alkenyl, $O(C_2-C_4)$ alkoxy, $O(C_1-C_4)$ alkyl-COO—, CN, or CONR11R12, wherein R11 is H or $(C_1-C_4)$ alkyl and R12 is H or $(C_1-C_4)$ alkyl.

In some embodiments, the compound is selected from the following group of compounds:

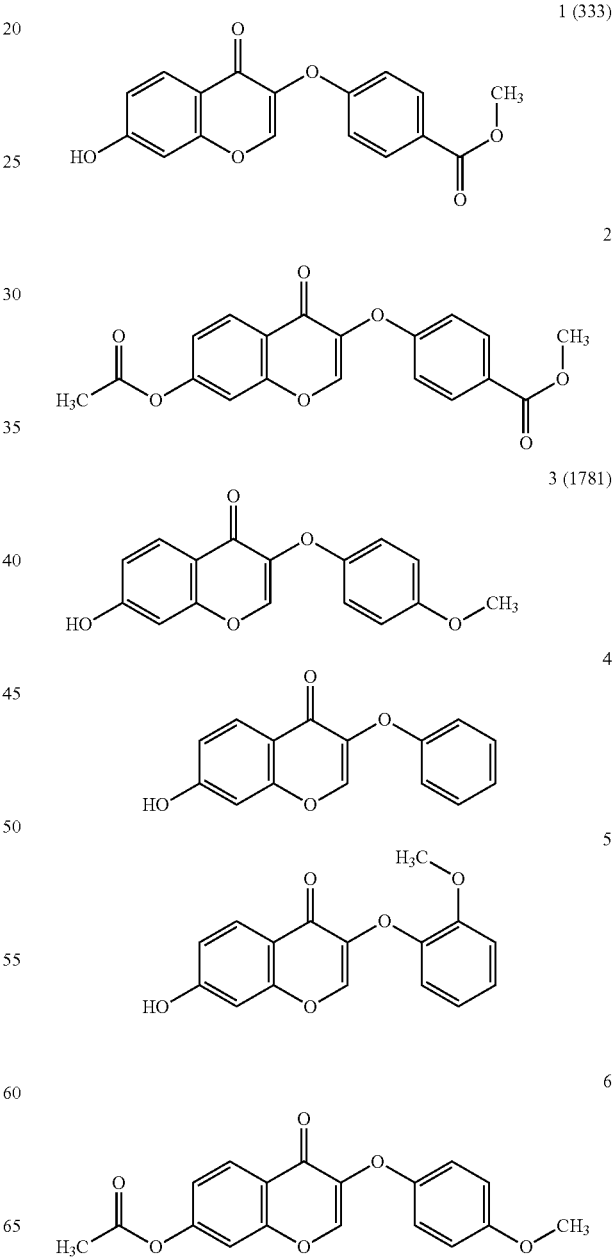

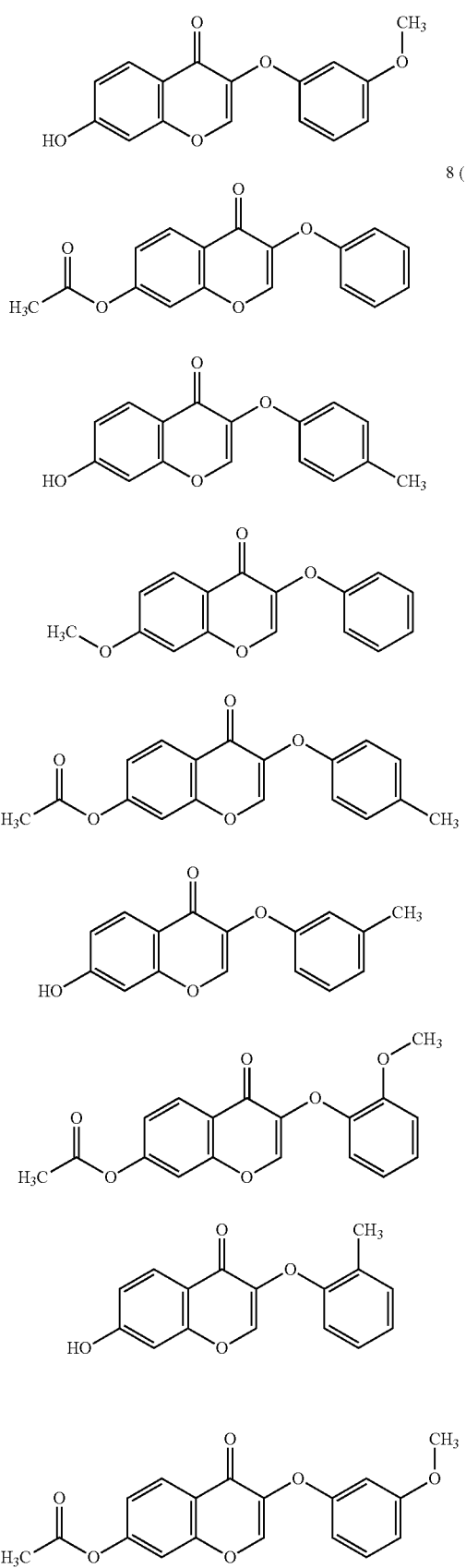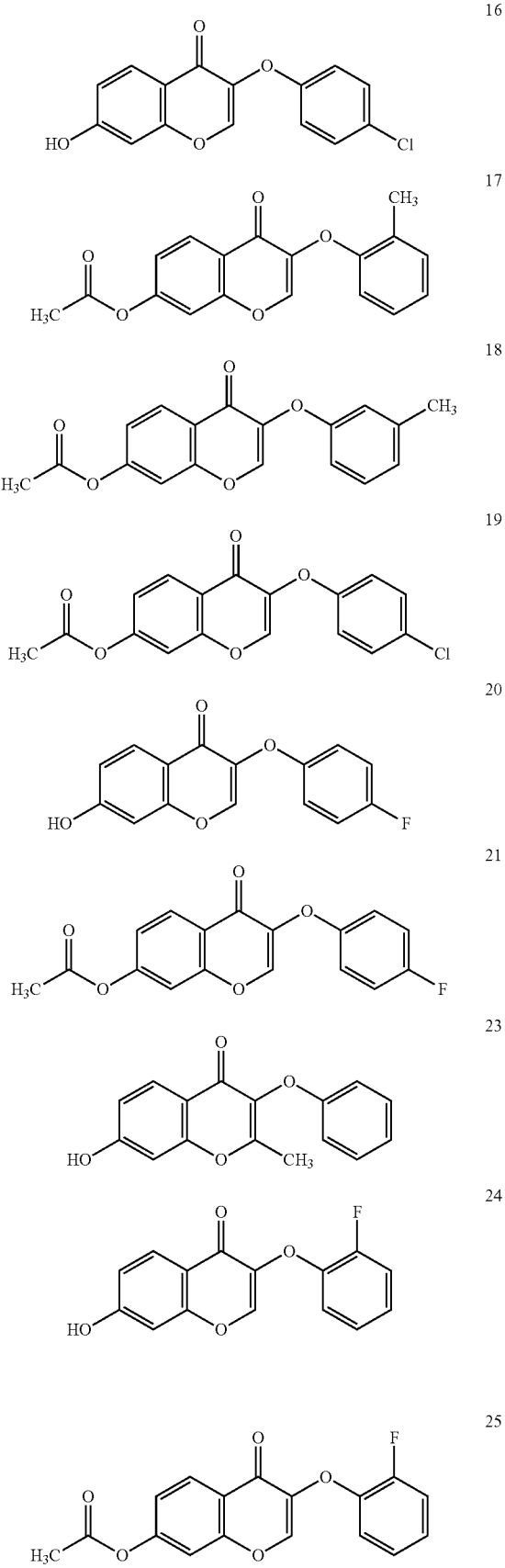

27

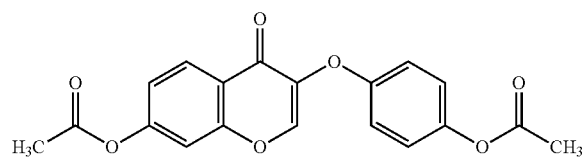

28

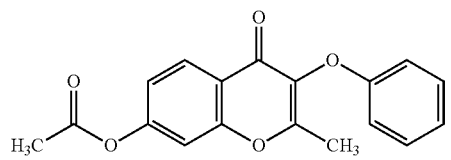

29

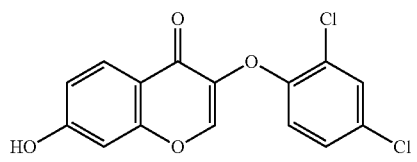

30

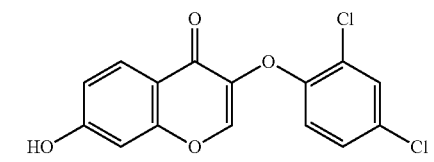

31

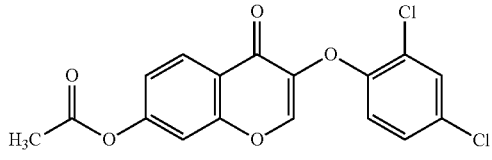

32

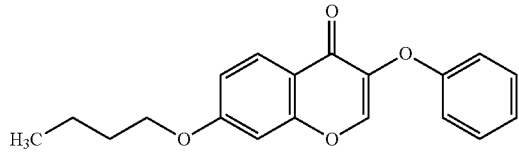

33 (276)

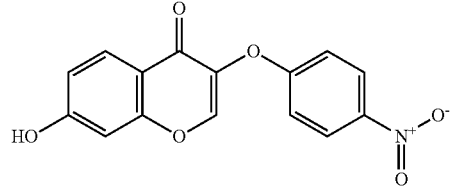

34

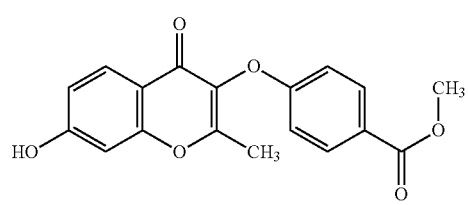

35

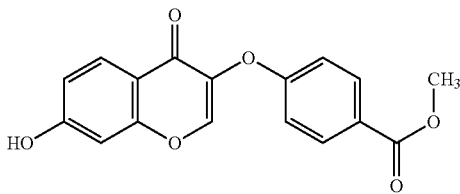

Use of Benzopyran Derivatives

In one embodiment of the present disclosure the benzopyran derivatives are used in the treatment of patients with disorders with an etiology associated with or comprising excessive cytokine release, particularly IL-6, IL-1β, IL-12 and IL-23 release, e.g. in a wide variety of inflammatory states and diseases such as rheumatoid arthritis, osteoarthritis, septic shock, psoriasis, atherosclerosis, inflammatory bowel disease, Crohn's disease, Alzheimer's Disease and asthma. In an alternative embodiment of the present disclosure the benzopyran derivatives are used to inhibit the release of cytokines and/or as functional antagonists of cytokines. In a specific embodiment, the benzopyran derivatives are used to inhibit the release of IFNγ, IL-1β, IL-6, IL-12, IL-17 and IL-23 and/or as functional antagonists of these cytokines. In an embodiment the compounds of the present disclosure may be used in the prophylaxis or treatment of diseases and medical conditions in general having an etiology associated with the increased or prolonged stability or translation of mRNAs which contain one or more mRNA instability sequences, and which on prolonged or inappropriate expression typically give rise to undesirable effects, e.g. unwanted inflammatory response or cancer cell growth.

Compounds of the present disclosure may be used in connection with diseases and medical conditions associated with any of the genes mentioned above or described in the listed publications, which comprise mRNA instability sequences.

Examples of diseases and medical conditions which may be treated or prevented by use of the present disclosure include acute and chronic inflammation, autoimmune diseases, respiratory diseases, infectious diseases and transplant rejection, as well as, neuronal inflammation, Alzheimer's disease and cardiovascular diseases.

Other examples of diseases and medical conditions which may be treated or prevented by use of the present disclosure include pathological conditions associated with abnormal cell proliferation, such as cancer. The pathological conditions include the abnormal cell proliferation of malignant cells of various tissues and/or organs, comprising, with no limitation being implied, muscle, bone or connective tissues, the skin, brain, lungs, sex organs, the lymphatic or renal systems, mammary or blood cells, liver, the digestive tract, pancreas and thyroid or adrenal glands. These pathological conditions can also include solid tumors, cancers of the ovary, breast, brain, prostate, colon, stomach, kidney or testicles, Kaposi's sarcoma, cholangioma, chorioma, neuroblastoma, Wilms' tumor, Hodgkin's disease, melanomas, multiple myelomas, lymphatic leukemias and acute or chronic granulocytic lymphomas.

In a related embodiment the compounds of the present disclosure which induce degradation or prevent translation of mRNA that contains one or more mRNA instability sequences are provided for use as pharmaceuticals, e.g. for use in the prophylaxis or treatment of diseases and medical conditions in general having an etiology associated with the increased or prolonged stability of mRNAs which contain one or more mRNA instability sequences, and which on prolonged or inappropriate expression typically give rise to undesirable effects, e.g. cancer cell growth or an unwanted inflammatory response.

Treatment with compounds of this disclosure advantageously leads to degradation of the mRNAs of such genes, resulting in the down-regulation or "switching off" of gene expression. Thus for example, they may be use for treatment and prevention of oncogene mediated cancers and malignant diseases, to treat or prevent tumor growth and metastasis invasion in general, and to prevent or reverse multidrug resistance and thereby facilitate cancer and tumor treatment with conventional, e.g. cytotoxic, anti-cancer agents.

Characteristically when the benzopyran derivatives are used to prevent or reverse multidrug resistance of tumor and other malignant cells, they are used in combination with cytostatic or cytotoxic agents.

The benzopyran derivatives according to the present disclosure may be used either alone or in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic agents.

Compositions of Compounds of the Present Disclosure

The present disclosure encompasses pharmaceutical compositions capable of being delivered and remain resident in a patient, the formulation and administration of such compositions known in the art.

In one embodiment of the present disclosure there is provided compositions comprising one or more benzopyran derivative of Formula I and one or more non-toxic pharmaceutically acceptable carriers and/or diluents and/or adjuvants and, if desired, other active ingredients. As indicated above such compositions are used in the treatment of various conditions in mammals, including humans.

Suitable pharmaceutical compositions comprising the compounds of the present disclosure as an active ingredient and that can be used especially in the treatment of the diseases mentioned above include compositions for enteral, such as nasal, buccal, rectal or especially oral, administration and parenteral, such as intravenous, intramuscular or subcutaneous, administration to warm-blooded animals, especially human beings. The compositions comprise the active ingredient on its own or preferably together with a pharmaceutically acceptable carrier. The dosage of the active ingredient depends on the disease to be treated, and on species, age, weight and individual condition, individual pharmacokinetic conditions, and the mode of administration. The dosage can be readily determined by a worker skilled in the art using standard methods in light of the above considerations.

The pharmaceutical compositions may comprise from approximately 1% to approximately 95% active ingredient, forms of administration in single dose form preferably comprising from approximately 20% to approximately 90% active ingredient and forms of administration that are not in single dose form preferably comprising from approximately 5% to approximately 20% active ingredient. Unit dose forms are, for example, dragées, tablets, ampoules, vials, suppositories or capsules. Other forms of administration are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions are prepared in a manner known per se, for example by means of conventional mixing, granulating, confectioning, dissolving or lyophilizing procedures.

Solutions of the active ingredient, and also suspensions or dispersions, especially isotonic aqueous solutions, dispersions or suspensions, are preferably used, it being possible, for example in the case of lyophilized compositions that contain the active ingredient alone or together with a carrier, for example mannitol, for such solutions, suspensions or dispersions to be made up prior to use. The pharmaceutical compositions may be sterilized and/or may comprise excipients, for example preservatives, stabilizers, wetting agents and/or emulsifiers, solubilizers, salts for regulating the osmotic pressure and/or buffers, and are prepared in a manner known per se, for example by means of conventional dissolving or lyophilizing procedures. The solutions or suspensions may comprise viscosity-increasing substances, such as sodium carboxymethylcellulose, dextran, polyvinylpyrrolidone or gelatin.

Suspensions in oil comprise an oil component being vegetable, synthetic or semi-synthetic oils customary for injection purposes. There may be mentioned as such, especially liquid fatty acid esters that contain as acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Labrafil M 1944 CS" (unsaturated polyglycolised glycerides prepared by alcoholysis of apricot kernel oil and consisting of glycerides and polyethylene glycol ester; Gattefossé, France), "Labrasol" (saturated polyglycolised glycerides prepared by alcoholysis of TCM and consisting of glycerides and polyethylene glycol ester; Gattefosse, France) and/or "Miglyol 812" (triglyceride of saturated fatty acids with a chain length of C8 to C12, Hills AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into, for example, ampoules or vials and to sealing the containers.

Pharmaceutical compositions for oral administration can be obtained, for example, by combining the active ingredient with one or more solid carriers, if desired granulating a resulting mixture, and processing the mixture or granules, if desired, and if necessary by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colorings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticizer, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents, for example of the polyoxyethylene sorbitan fatty acid ester type, may also be added.

Other oral forms of administration are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are suitable especially aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, can also be in the form of a lyophilisate and can be made into a solution prior to parenteral administration by the addition of suitable solvents.

The compounds for use in the disclosure can be administered, prophylactically or therapeutically, as such or in the form of pharmaceutical compositions, preferably in an amount effective against the said diseases, to a warm-blooded animal, for example a human being, requiring such treatment, the compounds being used especially in the form of pharmaceutical compositions. In such treatment an individual of about 70 kg body weight will be administered a daily dose of from approximately 0.1 g to approximately 5 g, preferably from approximately 0.5 g to approximately 2 g, of a compound.

The disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present disclosure may be employed in conjunction with other therapeutic compounds.

Activity of Benzopyran Derivatives

Anti-Inflammatory Activity

As demonstrated herein, compounds of the present disclosure may exhibit anti-inflammatory activity, for example due to their ability to inhibit release of cytokines or act as antagonists of cytokine activity.

In Vitro Methodology

One exemplary method of measuring the ability of the benzopyran derivatives of the present disclosure to inhibit cytokine release is performed by monitoring the release of cytokines from cells that have been stimulated to release cytokines either in the presence or the absence of the test compound. Lipopolysaccharide (LPS) is one type of stimulant that can be used to induce cytokine release although other stimulants may be used in this assay. Following treatment of the cells in culture by the stimulant, with and without the test compound, the cells are incubated for an appropriate period of time and then the culture medium and cell lysates are collected. Assays are then performed using the isolated media and lysates to determine the amount of cytokine (e.g. IL $1\beta$ (medium and lysate), IL 6 (medium), TNF$\alpha$ (medium) and PGE2 (medium and lysate)) present in each sample. In order to ensure that the compounds are also non-toxic to the cells, lactate dehydrogenase (LDH) activity (medium and lysate) and DNA (lysates) are also analyzed. IL $1\beta$, IL 6 and TNF $\alpha$ assays can be determined using commercially available ELISA kits (Cistron), PGE2 can be measured using a standard RIA and DNA fluorimetrically using DAPI (4',6 diamidino 2 phenylindole.2HCl). It should be recognized that this test is not limited by the assay(s) used to quantify the cytokines, LDH release or DNA since multiple assays are known and the assays listed herein are not intended to limit the scope of the present disclosure. A reduction in the amount of cytokine in the medium from the treated cells in comparison to the medium from the untreated cells is indicative of the ability of the test compound to inhibit release is unchanged in the treated versus the untreated cells.

Another exemplary method of measuring the ability of the benzopyran derivatives of the present disclosure to inhibit cytokine release is performed by comparing cytokine release from cells stimulated in culture in the presence and absence of the test compound. In an example of such a method mononuclear cells are obtained and cultivated on tissue culture dishes with the test compound at various concentrations, Schnyder et al., Agents & Actions, 30, 350 362 (1990). The non-adherent lymphocytes are removed after 4 hrs by washing several times. Fresh medium, test compound and stimulant, for example lipopolysaccharide (LPS), are added and the monocytes incubated for a further day.

Purified IL 1, recombinant human IL 1 β (rhIL 1) or conditioned media collected from stimulated human monocytes, mouse macro¬phages or mouse cell line P388D1, cause characteristic changes in the secretory pattern of chondrocytes. In particular, a latent metalloproteinase is induced, whilst secretion of plasminogen activator is reduced. The property of the metallo¬proteinase or stromelysin has been described in detail, Chin et al., J. Biol. Chem. 260, 12367 12376 (1985), as has that of the plasminogen activator, Schnyder et al., Anal. Biochem. 200, 156 162 (1992). In performing the assay the pooled culture media are diluted 1:10 with fresh medium and added to confluent rabbit chondrocytes. Metalloproteinase activity in the chondrocyte culture medium is assayed after a further 2 days using standard techniques known to workers skilled in the art. One example of a technique for measuring metalloproteinase activity is provided in Example 6 of the present disclosure. Compounds having the ability to reduce cytokine release will decrease induction of metalloprotease activity in the chondrocytes that are pooled with the culture media from treated cells in comparison to those pooled with the culture media from untreated cells.

In order to determine the antagonistic effects of the benzopyran derivatives of the present disclosure a cytokine is added to cultured cells that are known to respond to the cytokine and their response is monitored in the presence and the absence of the test compound. Example 7 of the present disclosure demonstrates one example of such a test in which chondrocytes are used. As described herein, chondrocytes will respond to IL-1 by an increase in metalloproteinase activity. A test compound is demonstrated to have an antagonistic effect if the metalloproteinase activity is decreased in the presence of the test compound in comparison to the activity in its absence.

In Vivo Methodology

One known animal model of an inflammatory response is LPS-induced fever in rats. An LPS suspension is injected in rats. At a certain time interval following injection the body temperature of the rat is measured and following the next interval of time the test compound is administered. At the end of the third time interval the body temperature is measured again. The temperature increment shown by the untreated controls can be taken as 100% and that in the treated group can be expressed as a percentage of this value. The ED50 is the dose causing a 50% inhibition of the temperature increase determined in the control rats. Compounds of the present disclosure typically have an ED50 in this assay of from about 0.1 to about 1 mg/kg.

A recognized animal model of inflammation is carrageenan induced paw edema in the rat. The test compound is administered to the rats one hour prior to the carrageenan injection by subplantar injection into one hind paw. The swelling of the paw is measured. A control reading is taken immediately after the injection, and the swelling is measured after 3 and 5 hrs. The mean value of the 3 and 5 hour reading is taken after deduction of the control reading, and the values obtained from the treated animals are expressed as a percentage of the value obtained from non treated controls. The ED50 is the dose causing a 50% inhibition of the carrageenan induced swelling after 3 hr. Compounds of the disclosure typically have ED50's in this assay of from about 0.5 to about 1 mg/kg.

It should be readily appreciated that the tests described herein are examples of standard tests that can be used to measure the activity of the compounds of the present disclosure. A wide variety of tests for measuring anti-cancer or anti-neoplastic activity, ability to increase or restore drug sensitivity, ability to induce mRNA degradation and anti-inflammatory activity are well known and can be used to demonstrate the characteristics of the benzopyran derivatives of the present disclosure.

Anti-Cancer Activity

As IL-6 is implicated in cancer the benzopyran derivatives of the present disclosure may be useful in the treatment of various types of cancer through their ability to inhibit the growth of cancer cells, the ability to increase or restore sensitivity of a cancer cell to one or more anti-neoplastic/cytotoxic drugs; and the ability to induce mRNA degradation. Compounds of the present disclosure can be assayed to demonstrate the extent of their activities using standard techniques well known to workers skilled in the art. Exemplary testing methods are outlined herein and are not intended to limit the scope of the present disclosure.

Compounds of the present disclosure may be tested for their activity as anti-cancer agents in cell or in vivo assays substantially as described herein or in variants of such assays using appropriate cell lines and conditions as would be readily appreciated by a worker skilled in the art. Compounds of this disclosure may be assayed for anti-cancer activity by conventional methods, including for example, the methods described below.

In Vitro Methodology

Cytotoxicity may be measured using a standard methodology for adherent cell lines such as the microculture tetrazolium assay (MTT). Details of this assay have been published (Alley, M C et al, Cancer Research 48:589-601, 1988). Exponentially growing cultures of tumor cells such as the HT-29 colon carcinoma or LX-1 lung tumor are used to make microtiter plate cultures. Cells are seeded at 3000 cells per well in 96-well plates (in 150 µl or media), and grown overnight at 37° C. Test compounds are added, in 10-fold dilutions varying from 10-4M to 10-10M. Cells are then incubated for 72 hours. To determine the number of viable cells in each well, the MTT dye is added (50 µl or 3 mg/ml solution of 3-(4,5-dimethylthiazol-2-yl)-2,5-diphenyltetrazolium bromide in saline). This mixture is incubated at 37° C. for 5 hours, and then 50 µl of 25% SDS, pH2 is added to each well. After an overnight incubation, the absorbance of each well at 550 nm is read using an ELISA reader. The values for the mean±SD of data from replicated wells are calculated, using the formula % T/C (% viable cells treated/control). 1 OD of treated cells OD of control cells× 100+% T/C. The concentration of test compound which gives a T/C of 50% growth inhibition is designated as the IC50 value.

An alternative method of evaluating anti-cancer activity of the compounds of the present disclosure involves determining the effect of a test compound on the viability of cancer cells. Exponentially growing cancer cells are treated with various concentrations of the test compound. Examples of cell lines that can be used in this method are MCF-7, MDA-MB-231, HCT116, KB 31, HCT-15, and DU 145 which are readily obtainable from ATCC, Bethesda, Md., U.S.A. The cells are further incubated for 24 h, 48 h and 96 h and stained with a molecule that allows a distinction between viable and non-viable cells, for example YOPRO-1 as described by T. Idziorek, (Idziorek, Estaquier et al. (1995). YOPRO-1 permits cytofluorometric analysis of programmed cell death (apoptosis) without interfering with cell viability. J Immunol Methods. 185: 249-258). The percent viability is then compared to control cells. A decrease in viability (shown as an increase in % loss of viability in FIG. 1) in the treated cells in comparison to the control cells is indicative of anti-cancer activity.

Another method of evaluating anti-cancer activity of the compounds of the present disclosure involves monitoring the effect of the compounds on cell cycle progression. Exponentially growing cancer cells are treated with various concentrations of the test compound. The cells were further incubated for 24 h, 48h and 96 h. Cells are then lysed and dsDNA is stained with YOPRO-1 as described by T. Idziorek Idziorek, Estaquier et al. (1995). YOPRO-1 permits cytofluorometric analysis of programmed cell death (apoptosis) without interfering with cell viability. J Immunol Methods. 185: 249-258. Fluorescence measurements are carried out essentially as described in Singer, Jones et al. (1997). Characterization of PicoGreen reagent and development of a fluorescence-based solution assay for double-stranded DNA quantitation, Anal Biochem. 249: 228-238, and values compared to control cells. A decrease in relative growth of treated cells in comparison to untreated cells is indicative of anti-cancer activity.

In an exemplary method of evaluating the inhibitory effect of the compounds of the present disclosure on the growth of cancer cells, cells are treated with the test compound and gene expression levels are measured in comparison to untreated cells. For example, human breast cancer cells, MCF-7, are cultured at 5% CO2 and 37° C. in MEM containing 0.1 mM non-essential amino acids, 2 mM L-glutamine and 10% FBSe. Total RNA from cells approximately 50% confluent is isolated using a Qiagen RNeasy Midi™ kit according to manufacturer's instructions. Total RNA is harvested at various times in the presence and absence of the benzopyran derivative being evaluated. RNase protection analysis is performed using the RiboQuant™ Multi-Probe Ribonuclease Protection Assay System from Pharmingen utilizing hAPO-2c and custom human (bclx L/S, p53, GADD45, c-fos, bax, bcl-2, c-myc, L32 and GAPDH) templates, T7 RNA polymerase and [α-32P]UTP (as per manufacturer's instructions). Quantitation of the expression levels is performed using a Storm 860™ Molecular Dynamics Phosphoimager with ImageQuant™ software. Decreased expression of a proto-oncogene, for example bcl-2, in treated cells in comparison to untreated cells is indicative of anti-cancer activity.

In Vivo Methodology

Compounds of this disclosure may be further tested in pre-clinical assay for in vivo activity which is indicative of clinical utility. Such assays are conducted with nude mice into which tumor tissue, preferably of human origin, has been transplanted (xenografted), as is well known in this field. Test compounds are evaluated for their anti-tumor efficacy following administration to the xenograft-bearing mice.

For example, human breast tumors (MX-1) which have been grown in athymic nude mice are transplanted into new recipient mice, using tumor fragments which are about 50 mg in size. The day of transplantation is designated as day 0. Six to ten days later, mice are treated with the test compounds given as an intravenous injection or orally, in groups of 5-10 mice at each dose. Compounds are given every other day, for 3 weeks.

Tumor diameters and body weights are measured twice weekly. Tumor volumes were calculated using the diameters measured with Vernier calipers, and the formula: (Length×width$^2$)±2=mm$^3$ of tumor volume, with mean tumor volumes being calculated for each treatment group, and T/C values determined for each group relative to the untreated control tumors.

Increasing or Restoring Drug Sensitivity

Certain benzopyran derivatives according to the present disclosure may increase or restore the sensitivity of a cancer cell to one or more anti-neoplastic/cytotoxic drugs. A suitable cell-based assay for assessing the ability of a candidate compound to restore sensitivity of cancer cells to anti-neoplastic/cytotoxic drug substances in vitro is as follows. Cancer cell lines (CCL), e.g. from human small cell carcinoma of the lung, resistant to one or more cancer therapeutic drug substances (CTDS) selected from the group comprising Daunorubicin (DR); Vincristine (VC); Adriamycin (AM); Etoposide (ET); Tenoposide (TE); Colchicine (CC); and Taxol are developed in accordance with the methods described by Twentyman et al., Br. J. Cancer, 54, 253 (1986).

Sensitivity of resistant sub-lines (CCL-R) is compared with parental sensitive lines (CCL-S) by assaying inhibition of cell growth during continuous CTDS exposure, e.g. in the case of a DR-resistant line (CCL-DRR) by comparing growth of CCL-DRS and CCL-DRR lines in the presence of DR contained in the growth medium ab initio. For the purpose, cell proliferation is measured by cell counting using an electronic cell counter, counting being effected close to the termination of the exponential growth phase. CCL-R lines are selected for which the IC80 (drug concentration, e.g. DR concentration, required to reduce final cell number to 20% of that for non-CTDS (e.g. DR) treated controls is >80×, preferably >100×, greater than that of the parental CCL-S lines.

Sensitivity of selected CCL-R lines to CTDS (e.g. DR) in the presence or absence of test benzopyran derivatives is then performed, employing cell counting as a measure of proliferation as described above. For this purpose cells are cultured ab initio in the presence of varying concentrations of both CTDS and test benzopyran derivatives. For screening, concentrations of the latter are chosen which do not themselves cause a significant reduction in proliferation. Appropriate concentrations are established by culturing CCL-S and CCL-R in the presence of varying concentrations of benzopyran derivatives in the absence of CTDS. Benzopyran derivatives are routinely tested at concentrations of from 0.01 to 50 µg/ml, in particular 0.1 to 10.0 µg/ml, e.g. at concentrations of 0.01, 0.02, 0.05, 0.1, 0.2, 0.5, 1.0, 2.0, 5.0, 10.0 and 50 µg/ml. The ratio of CTDS (e.g. DR) required to inhibit cell proliferation by 50% in the absence of test benzopyran derivatives (IC50-CS) compared with that obtained in the presence of test benzopyran derivatives (IC50+CS) is taken as a measure of increased sensitivity of the CCL-R line to CTDS which has been induced by the benzopyran derivatives. Stability of the CCL-R line used is ensured by cross checking its sensitivity to CTDS with that previously established.

Additional procedures for assessing utility in restoring sensitivity of cancer cells to anti-neoplastic/cytotoxic, drug substances, including in vivo procedures are described in EP 0296122 B, the relevant disclosures of which are incorporated by reference in the teaching of the present application.

The compounds of the disclosure may have pharmacological properties. In particular, they may show inhibition of cytokine gene expression, inhibiting cytokine release and working as functional antagonists. To gain a better understanding of the disclosure described herein, the following examples are set forth. It should be understood that these examples are for illustrative purposes only. Therefore, such examples should not limit the scope of this disclosure in any way.

EXAMPLE 1

Cytokine Release from THP 1 Cells Measured by ELISA

The THP 1 cell line is generally available and is described by Tsuchia et. al. Tsuchiya, Yamabe et al. (1980). Establishment and characterization of a human acute monocytic leukemia cell line (THP-1). Int J Cancer. 26: 171-176.

900 µl THP 1 cells (0.5×106 cells) together with 100 Uγ interferon/0.9 ml RPMI 1640 medium (containing 2 mM L glutamine and 5% heat inactivated fetal calf serum) are pipetted into 24-well culture plates. 100 µl of the compound to be tested are then added. After 3 hours at 37° C. in 5% $CO2/95\%$ air, 10 µl lipopolysaccharide (LPS) 500 µg/ml is added and the incubation continued for a further 24 hours. Appropriate controls (with and without stimulus, solvent) are also included. The media are then removed and clarified by centrifugation at 1000 g for 10 min. Samples are stored at 80° C. until the determinations can be made. IL 1β, IL 6 IL-12, and IL-23 assays are determined using commercially available ELISA kits. In these tests, the compounds of the disclosure may inhibit IL-1β, IL-6, IL-12 and IL-23 release at a concentration of about 10 to 50 µM. The compounds are non-toxic based on resazurin measurements as described in Didiot, Hewett et al. (2013). Identification of cardiac glycoside molecules as inhibitors of c-Myc IRES-mediated translation. J Biomol Screen. 18: 407-419.

TABLE I

Effect of benzopyran derivatives 333, 1781 and 1782 at various concentrations on IL-6 release from THP 1 Cells measured by ELISA. RAA: radicicol analog A.

| Cpd f.c. [µM] | 333 | 1781 | 1782 | RAA |
|---|---|---|---|---|
| | | % control | | |
| 10 | 48 | 74 | 56 | 3 |
| 40 | 43 | 64 | 57 | 2 |
| 100 | 35 | 55 | 28 | 3 |

TABLE II

Effect of benzopyran derivatives 333, 1781 and 1782 at 10 µM on Cytokine release from THP 1 Cells measured by ELISA.

| Cytokine Cpd | IL-6 | IL-1β | IL-23 |
|---|---|---|---|
| | % control at 10 µM | | |
| 333 | 48 | 49 | 68 |
| 1781 | 74 | 100 | 100 |
| 1782 | 56 | 100 | 93 |

EXAMPLE 2

Cytokine Release from Peripheral Blood Mononuclear Cells Measured by ELISA

Mononuclear cells are obtained from the blood of healthy volunteers via centrifugation and cultivated on tissue culture dishes with the test compound at various concentrations Schnyder, Bollinger et al. (1990). Inhibition of interleukin-1 release by IX 207-887. Agents Actions. 30: 350-362. Fresh human mononuclear cells were isolated on Ficoll-Paque gradient and washed several times. Fresh medium, test compound and LPS (10 µg/ml) or PHA (5 µg/ml) as stimulant are added and the monocytes incubated for a further day. The media are then removed and clarified by centrifugation at 1000×g for 10 min. Samples are stored at 80° C. until the determinations can be made. IFNγ, IL 1β, IL 6, and IL-17 are determined using commercially available ELISA kits.

TABLE IIa

IL-6 release from PBMCs measured by ELISA (% control)
IL-6

| [µM] | 333 | 1781 | 1782 | RAA |
|---|---|---|---|---|
| 2.5 | 121 | 115 | 106 | 10 |
| 5 | 158 | 127 | 139 | 9 |
| 10 | 176 | 83 | 89 | 11 |
| 20 | 68 | 57 | 61 | 11 |

TABLE IIb

IL-1β release from PBMCs measured by ELISA (% control)
IL-1β

| [µM] | 333 | 1781 | 1782 | RAA |
|---|---|---|---|---|
| 2.5 | 105 | 136 | 123 | 4 |
| 5 | 91 | 137 | 115 | 4 |
| 10 | 58 | 104 | 109 | 4 |
| 20 | 45 | 104 | 89 | 4 |

TABLE IIc

IFNγ release from PBMCs measured by ELISA (% control)

| IFNγ | % control (24 h) | | |
|---|---|---|---|
| [µM] | 333 | 1781 | 276 |
| 5 | 43 | 75 | 100 |

TABLE IId

IL-17 release from PBMCs measured by ELISA (% control)

| IL-17 | % control (48 h) | |
|---|---|---|
| [µM] | 276 | 333 |
| 2.5 | 79 | 93 |
| 5 | 46 | 80 |
| 10 | 57 | 41 |

EXAMPLE 3

Reporter Gene Assays for Compounds which Destabilize mRNA

The basic principle of a reporter gene assay for determining compounds that destabilize mRNA is described in detail in WO 00/39314. A number of these assays for various drug targets have been developed and were tested with the compounds described in this disclosure. For THP-1 cells, compound is added at the time of the addition of LPS and luciferase measurements are taken 24 hours later or as indicated. For other cell lines, cells were plated in 96 well plates at $5*10^5$ cells per 100 ul per well and incubated over night at 37° C. Compounds were then added and luciferase activity was measured after 24 hours. The activity was compared to other mRNA stability assays established for a range of other drug targets and found to be specific for IL-6, IL-12p40 and IL-23p19. Luciferase activity in the IL-6, IL-12 and IL-23 assays was inhibited by 10 µM benzopyran derivatives by >40% (Table IV).

TABLE III

Activities of benzopyran derivatives on various mRNA stability assays at 10 µM.

| | Conc. | Assay | (% inhibition) | | | | | | | | |
|---|---|---|---|---|---|---|---|---|---|---|---|
| Cpd | [µM] | IL-6 | IL-12 p40 | IL-23 p19 | c-myc | Htt | SNCA | PTP-1B | APP | TNFa | DNMT1 |
| 333 | 10 | IC$_{50}$: 2.51 µM | 72 | 76 | n.a. | n.a. | n.a. | n.a. | n.a. | n.a. | n.a. |
| 1781 | 10 | 84 | 62 | 41 | n.a. | n.a. | n.a. | n.a. | n.a. | n.a. | n.a. |
| 1782 | 10 | n.a. | n.a. | n.a. | n.a. | n.a. | n.a. | n.a. | n.a. | n.a. | n.a. |
| RAA | 10 | IC$_{50}$: 128 n | 64 | 94 | n.a. | 35 | 25 | n.a. | 5 | n.d. | 19 |

(n.a.: no activity, n.d.: not determined)

EXAMPLE 4

Effect on Cytokine mRNA Levels

Total RNA was isolated at t=24 h from IFN-γ/LPS-stimulated THP-1 cells exposed to compounds (10 µM) or DMSO (solvent control) for 24 and 40 h, using the RNeasy Midi Kit (Qiagen), according to the manufacturer's instructions, and eluted in DEPC-treated Milli-Q H2O. Quantity and purity of RNA were determined by absorbance at 260 and 280 nm.

For RT-PCR analysis, 1 µg of total RNA was reverse transcribed using AMV reverse transcriptase (Life Sciences Inc., St. Petersburg, Fla.), then amplified by the PCR method. Each PCR reaction also contained a set of β-actin primers as internal control. The levels of the expected PCR product were compared to the constant levels of β-actin. The size of the PCR products was compared to MspI digested pBR322 standards (New England Biolabs). PCR products were analyzed on a 4% agarose gel.

Nucleotide sequences for the oligonucleotide 5' and 3' primers, respectively, were:

TABLE V

Nucleotide sequences for the oligonucleotide 5' and 3' primers

| | 5' | 3' |
|---|---|---|
| β-actin | ATGGGTCAGAAGGATTCCTA | AGAGGCGTACAGGGATAGCAC |
| IL-6 | AGTAACATGTGTGAAAGCAG | CAGGAACTGGATCAGGACTT |

As shown in Table VI the compounds did not have an effect on mRNA levels and are thus believed to affect translation rather than mRNA stability.

TABLE VI

Effect of benzoypyranes on cytokine mRNA levels in THP-1 cells IL-6 mRNA analysis

| Cell Treatment | Compound | % ctrl |
|---|---|---|
| γIFN, 0h | — | 9 |
| γIFN/LPS, 24h | DMSO | 100 |
| γIFN/LPS, 24h | 333 | 94 |
| γIFN/LPS, 24h | 1781 | 92 |
| γIFN/LPS, 24h | 1782 | 93 |
| γIFN/LPS, 24h | 732 | 8 |

Compounds of the disclosure may therefore be used for the treatment of disorders with an etiology associated with or comprising excessive cytokine release, particularly IL-1β, IL-6, IL-12 and IL-23 release, e.g. in a wide variety of inflammatory states and diseases such as rheumatoid arthritis, osteoarthritis, septic shock, psoriasis, atherosclerosis, inflammatory bowel disease, Crohn's disease, Alzheimer's disease, and asthma, and neoplastic diseases.

For the above uses, the required dosage will of course vary depending on the mode of administration, the particular condition to be treated and the effect desired.

EXAMPLE 5 (FIG. 1)

Effect on LPS-Induced Cytokine Release in Mice

Compounds were evaluated on intra-peritoneal LPS-induced cytokine release measured in serum in the CD-1 mouse. Vehicle, Test item and positive control were administered 1 h before LPS injection as well 30 min post LPS injection (except as otherwise varied herein). In serum samples collected at 4 h post LPS injection, following cytokines were measured by multiplex on MSD 10 V-plex platform: TNF-alpha, IFN-gamma, IL-1beta, IL-2, IL-4, IL-5, IL-6, IL-10, IL-12, KC/GRO. All cytokines except IL-5 were induced by LPS injection (compared with saline injection). As for the effects of the test items, statistically significant effects by the higher doses of TI1 and TI2 were seen for IFN-gamma only. The positive control dexamethasone blocked induction of most cytokines.

Figure 2:
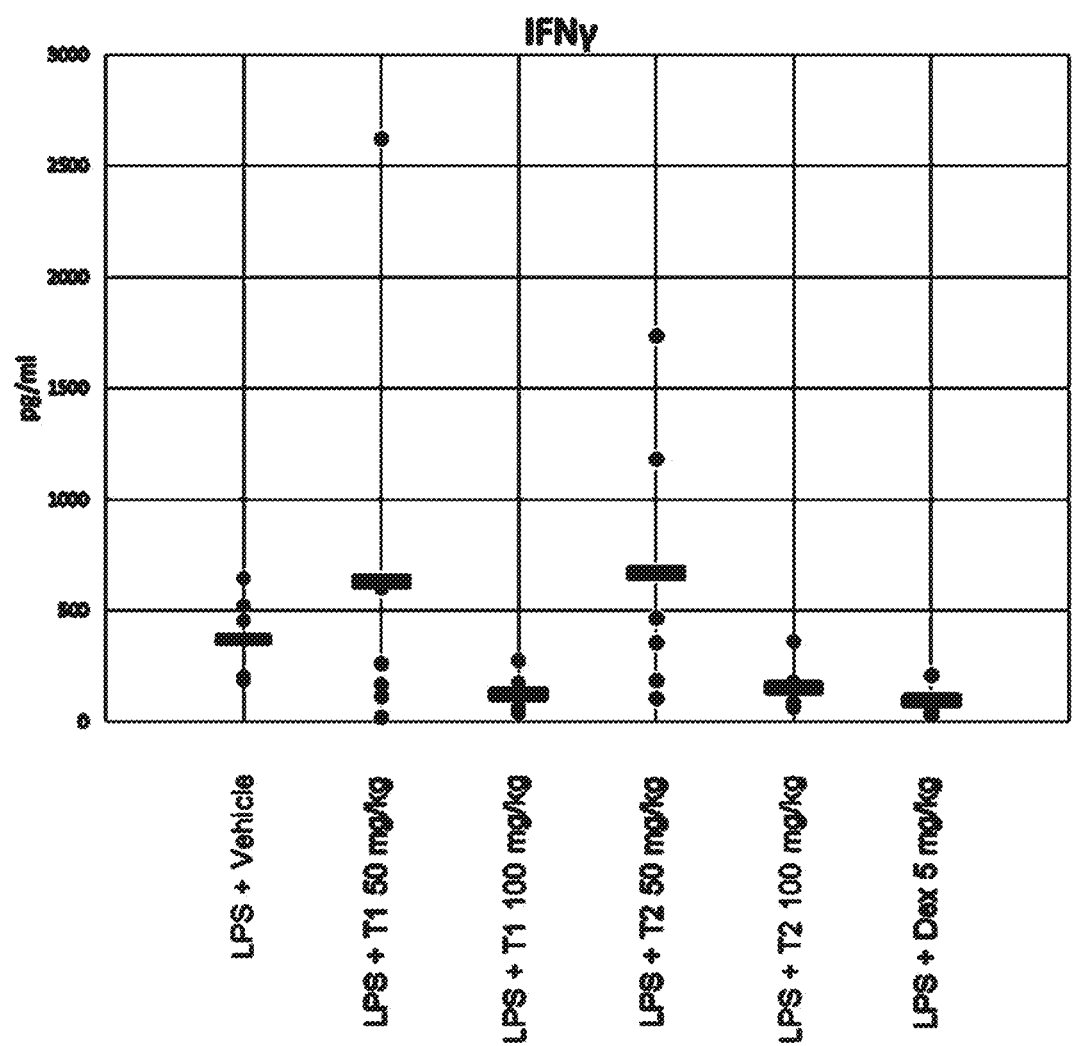
FIG. 2 is a vertical scatter plot illustrating the effect of test compounds 333 (TI1) and 1781 (TI2) on IFN-gamma levels in serum of various LPS treated mice.

Serum samples collected at 4h post LPS challenge were analyzed in duplicate wells using multiplex on MSD 10 V-plex platform. Pre-treatment with 333 or 1781 at 100 mg/kg significantly blocked LPS-induced increase in serum IFN-gamma level and there was a trend of effect on IL-12, IL-4 and TNF-alpha. FIG. 1: Effect of test compounds 333 (TI1) and 1781 (TI2) on IFN-gamma levels in serum of LPS treated mice. FIG. 2: Effect of test compounds 333 (TI1) and 1781 (TI2) on IFN-gamma levels in serum of LPS treated mice (values of individual animals)

EXAMPLE 6

Preparation of a Pharmaceutical Composition

Tablets, each comprising e.g. 50 mg of compound or a pharmaceutically acceptable salt, are prepared as follows:
Composition (10000 Tablets)

| active ingredient | 500.0 g |
|---|---|
| lactose | 500.0 g |
| potato starch | 352.0 g |

-continued

| | |
|---|---|
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

EXAMPLE 7

Preparation of a Pharmaceutical Composition

Film-coated tablet, each comprising 100 mg of benzopyran derivatives or a pharmaceutically acceptable salt are prepared as follows:
Composition (for 1000 Film-Coated Tablets)

| | |
|---|---|
| active ingredient | 100.0 g |
| lactose | 100.0 g |
| corn starch | 70.0 g |
| talc | 60.0 g |
| calcium stearate | 1.5 g |
| hydroxypropylmethylcellulose | 2.36 g |
| shellac | 0.64 g |
| water | q.s |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

EXAMPLE 8

Preparation of a Pharmaceutical Composition

Hard gelatin capsules, comprising 100 mg of active ingredient, for example benzopyran derivatives or a pharmaceutically acceptable salt are prepared, for example, as follows:
Composition (for 1000 Capsules)

| | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilized active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation. Soft gelatin capsules may be prepared using similar ingredients and procedures.

The test results reported in this document include tests on human cells and on cells and systems analogous to human systems. The compounds tested provide a representative sample of the class of compounds disclosed, and the core structure in Formulas I and II are believed to be responsible for the therapeutic effects disclosed here. Thus, the disclosed compounds, which share the core structure of the tested compounds, are predicted to have utility across the range of disclosed compounds. Organic groups include substituents that include at least one carbon atom.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A method comprising administering an effective amount of a compound to a patient to treat one or more of psoriasis, hemophagocytic lymphohistiocytosis, Alzheimer's disease, excessive inflammation due to cytokine release, respiratory diseases, or neuronal inflammation, in which the compound has the structure of formula I:

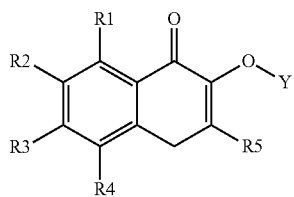

(I)

including pharmaceutically acceptable salts, pharmaceutically active metabolites, pharmaceutically acceptable solvates, pharmaceutically acceptable prodrugs, hydrates, stereoisomers thereof, and wherein: each of R1, R2, R3, R4, and R5 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, O($C_1$-$C_4$) alkyl, O($C_1$-$C_4$) alkenyl, O($C_2$-$C_4$) alkoxy, O($C_1$-$C_4$) alkyl-COO—, CN, alkyl-CONN, O-alkyl-CONH, or an organic group;

wherein, Y is:

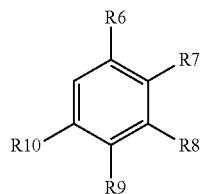

(II)

each of R6, R7, R9, and R10 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, O($C_1$-$C_4$) alkyl, O($C_1$-$C_4$) alkenyl, O($C_2$-$C_4$) alkoxy, O($C_1$-$C_4$) alkyl-COO—, CN, or an organic group; and R8 is $COOCH_3$.

2. The method according to claim 1 in which the compound is:

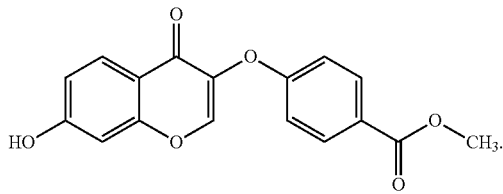

(IV)

3. The method according to 1 in which R1, R2, R4, R5, R6, R7, R9, R10 is H.

4. The method according to claim 3 in which R3 is $OCOCH_3$ or OH.

5. The method according to claim 1 in which each of R1, R2, R3, R4, and R5 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, O($C_1$-$C_4$) alkyl, O($C_1$-$C_4$) alkenyl, O($C_2$-$C_4$) alkoxy, O($C_1$-$C_4$) alkyl-COO—, CN, alkyl-CONH, or O-alkyl-CONH;

wherein, Y is:

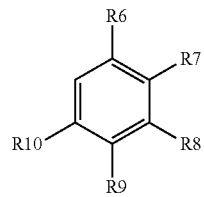

(II)

each of R6, R7, R9, and R10 are, independently from each other, H, OH, $NO_2$, $COOCH_3$, COOH, halogen, ($C_1$-$C_4$) alkyl, ($C_1$-$C_4$) alkenyl, ($C_1$-$C_4$) alkoxy, ($C_1$-$C_4$) alkyl-COO—, $OCOCH_3$, O($C_1$-$C_4$) alkyl, O($C_1$-$C_4$) alkenyl, O($C_2$-$C_4$) alkoxy, O($C_1$-$C_4$) alkyl-COO—, or CN.

6. The method according to claim 1 wherein R6, R7, R9, and R10 are H.

* * * * *

SEQUENCE LISTING

<160> NUMBER OF SEQ ID NOS: 8

<210> SEQ ID NO 1
<211> LENGTH: 5
<212> TYPE: RNA
<213> ORGANISM: Homo sapiens

<400> SEQUENCE: 1 auuua                                                                   5

<210> SEQ ID NO 2
<211> LENGTH: 7
<212> TYPE: RNA
<213> ORGANISM: Homo sapiens

<400> SEQUENCE: 2 uauuuau                                                              7

<210> SEQ ID NO 3
<211> LENGTH: 9
<212> TYPE: RNA
<213> ORGANISM: Homo sapiens

<400> SEQUENCE: 3 uuauuuaww                                                            9

<210> SEQ ID NO 4
<211> LENGTH: 9
<212> TYPE: RNA
<213> ORGANISM: Homo sapiens

<400> SEQUENCE: 4 auuuauuua                                                            9

<210> SEQ ID NO 5
<211> LENGTH: 20
<212> TYPE: DNA
<213> ORGANISM: Homo sapiens

<400> SEQUENCE: 5
atgggtcaga aggattccta                                                20

<210> SEQ ID NO 6
<211> LENGTH: 21
<212> TYPE: DNA
<213> ORGANISM: Homo sapiens

<400> SEQUENCE: 6
agaggcgtac agggatagca c                                              21

<210> SEQ ID NO 7
<211> LENGTH: 20
<212> TYPE: DNA
<213> ORGANISM: Homo sapiens

<400> SEQUENCE: 7
agtaacatgt gtgaaagcag                                                20

<210> SEQ ID NO 8
<211> LENGTH: 20
<212> TYPE: DNA
<213> ORGANISM: Homo sapiens

<400> SEQUENCE: 8
caggaactgg atcaggactt                                                20